(12) United States Patent
You et al.

(10) Patent No.: US 9,828,550 B2
(45) Date of Patent: Nov. 28, 2017

(54) POLYMERIZABLE COMPOSITION AND METHOD FOR MANUFACTURING LIQUID CRYSTAL DEVICE

(71) Applicant: LG CHEM, LTD., Seoul (KR)

(72) Inventors: Jung Sun You, Daejeon (KR); Dong Hyun Oh, Daejeon (KR); Sung Joon Min, Daejeon (KR); Kyung Jun Kim, Daejeon (KR); Dae Hee Lee, Daejeon (KR); Jun Won Chang, Daejeon (KR); Moon Soo Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/652,351

(22) PCT Filed: Dec. 16, 2013

(86) PCT No.: PCT/KR2013/011681
§ 371 (c)(1),
(2) Date: Jun. 15, 2015

(87) PCT Pub. No.: WO2014/092519
PCT Pub. Date: Jun. 19, 2014

(65) Prior Publication Data
US 2015/0368559 A1   Dec. 24, 2015

(30) Foreign Application Priority Data

Dec. 14, 2012  (KR) .................. 10-2012-0146671
Dec. 16, 2013  (KR) .................. 10-2013-0156781
Dec. 16, 2013  (KR) .................. 10-2013-0156783
Dec. 16, 2013  (KR) .................. 10-2013-0156785

(51) Int. Cl.
| C09K 19/56 | (2006.01) |
| C07C 69/602 | (2006.01) |
| G21K 5/08 | (2006.01) |
| C09K 19/54 | (2006.01) |
| G02F 1/1335 | (2006.01) |
| G02F 1/1337 | (2006.01) |
| C09K 19/02 | (2006.01) |
| G02F 1/00 | (2006.01) |
| G02F 1/1333 | (2006.01) |
| G02F 1/133 | (2006.01) |

(Continued)

(52) U.S. Cl.
CPC ............ *C09K 19/56* (2013.01); *C07C 69/602* (2013.01); *C08F 222/10* (2013.01); *C08L 33/14* (2013.01); *C09D 133/14* (2013.01); *C09K 19/02* (2013.01); *C09K 19/0208* (2013.01); *C09K 19/38* (2013.01); *C09K 19/42* (2013.01); *C09K 19/52* (2013.01); *C09K 19/542* (2013.01); *G02F 1/009* (2013.01); *G02F 1/13* (2013.01); *G02F 1/133* (2013.01); *G02F 1/1333* (2013.01); *G02F 1/1334* (2013.01); *G02F 1/1337* (2013.01); *G02F 1/133528* (2013.01); *G21K 5/08* (2013.01); *C08F 222/1006* (2013.01); *C09K 2019/0448* (2013.01); *C09K 2019/548* (2013.01); *G02F 2001/13345* (2013.01); *Y10T 428/10* (2015.01)

(58) Field of Classification Search
CPC ........ C09K 19/00; C09K 19/02; C09K 19/38; C09K 19/0208; C09K 19/42; C09K 19/52; C09K 19/56; C07C 69/602; C09D 133/14; G02F 1/00; G02F 1/009; G02F 1/00045; G02F 1/13; G02F 1/133; G02F 1/1333; G02F 1/33308; G02F 1/1134; G02F 1/1337
USPC .............. 427/58, 64, 66; 252/299.01, 299.4, 252/299.5; 349/101, 163, 182, 183, 19, 349/56, 86, 89, 90, 91, 92, 93, 94, 123, 349/125, 132, 149, 162, 166; 428/1.1, 428/1.2; 522/151, 152, 153, 154, 180, 522/181, 183; 525/212, 217, 220, 223, 525/230; 359/237; 378/137, 138; 396/457; 385/1, 4; 347/126; 348/751, 348/761, 766, 790, 794; 362/561
See application file for complete search history.

(56) References Cited

U.S. PATENT DOCUMENTS 4,891,152 A    1/1990  Miller et al.
5,372,745 A *  12/1994 Yoshinaga ......... C09K 19/3804
                                                   252/299.01

(Continued)

FOREIGN PATENT DOCUMENTS

CN    1070744 A    4/1993
CN    1670595 A    9/2005

(Continued)

OTHER PUBLICATIONS

International Search Report issued in International Application No. PCT/KR2013/011681 dated Mar. 12, 2014, 2 pages.

(Continued)

*Primary Examiner* — William Phillip Fletcher, III
(74) *Attorney, Agent, or Firm* — Rothwell, Figg, Ernst & Manbeck, P.C.

(57) ABSTRACT

Provided are a liquid crystal device, a composition capable of forming a liquid crystal layer, a method of manufacturing the liquid crystal device, a system for manufacturing the liquid crystal device, and a use of the liquid crystal device. The liquid crystal device is a device capable of exhibiting, for example, a normally white or black mode, which may exhibit a high contrast ratio and be driven with a low driving voltage, and exhibit excellent durability such as thermal stability. Such a liquid crystal device may be applied to various optical modulators such as a smart window, a window protective film, a flexible display device, an active retarder for displaying 3D images, or a viewing angle control film.

15 Claims, 14 Drawing Sheets

(51) Int. Cl.
*C09K 19/38* (2006.01)
*C09K 19/52* (2006.01)
*G02F 1/13* (2006.01)
*C09K 19/42* (2006.01)
*G02F 1/1334* (2006.01)
*C09D 133/14* (2006.01)
*C08L 33/14* (2006.01)
*C09K 19/04* (2006.01)
*C08F 222/10* (2006.01)

(56) References Cited

U.S. PATENT DOCUMENTS

| | | | |
|---|---|---|---|
| 5,384,067 A | 1/1995 | Doane et al. | |
| 5,450,220 A | 9/1995 | Onishi | |
| 5,566,008 A | 10/1996 | Yoshida et al. | |
| 5,691,795 A * | 11/1997 | Doane | C09K 19/02 349/115 |
| 5,750,213 A * | 5/1998 | Onishi | C09K 19/12 252/299.01 |
| 6,124,907 A | 9/2000 | Jones | |
| 6,791,658 B2 | 9/2004 | Maruyama et al. | |
| 6,897,936 B1 | 5/2005 | Li | |
| 7,072,008 B2 | 7/2006 | Iijima | |
| 7,919,648 B2 * | 4/2011 | Kato | C09K 19/0403 252/299.01 |
| 8,246,855 B2 * | 8/2012 | Hirai | C09K 19/2007 252/299.01 |
| 8,268,109 B2 | 9/2012 | Hwang et al. | |
| 2002/0054251 A1 | 5/2002 | Maruyama | |
| 2005/0007541 A1 * | 1/2005 | Sasada | C09K 19/0403 349/183 |
| 2007/0024970 A1 | 2/2007 | Lub et al. | |
| 2007/0269613 A1 | 11/2007 | Chien | |
| 2008/0198316 A1 | 8/2008 | Ichihashi | |
| 2009/0109375 A1 * | 4/2009 | Obata | G02B 1/08 349/74 |
| 2010/0007824 A1 | 1/2010 | Satoh | |
| 2011/0216274 A1 | 9/2011 | Kataoka | |
| 2012/0249928 A1 | 10/2012 | Kaihoko | |
| 2012/0287377 A1 | 11/2012 | Kim | |
| 2013/0196565 A1 | 8/2013 | Miyake | |
| 2014/0104544 A1 | 4/2014 | Goetz et al. | |
| 2015/0131033 A1 | 5/2015 | Min et al. | |
| 2015/0331264 A1 | 11/2015 | Min | |
| 2015/0338689 A1 | 11/2015 | Min | |

FOREIGN PATENT DOCUMENTS

| | | |
|---|---|---|
| CN | 101 429 436 A | 5/2009 |
| CN | 101429436 A | 5/2009 |
| CN | 102778772 A | 11/2012 |
| EP | 0 564 869 A1 | 10/1993 |
| EP | 0 636 921 A2 | 2/1995 |
| JP | H05-257126 A | 10/1993 |
| JP | H06-51351 A | 2/1994 |
| JP | H06-67162 A | 3/1994 |
| JP | H06-175113 A | 6/1994 |
| JP | H07-175051 A | 7/1995 |
| JP | H07-248489 A | 9/1995 |
| JP | H09-179102 A | 7/1997 |
| JP | H10-48602 A | 2/1998 |
| JP | 10-133016 A | 5/1998 |
| JP | H11-101964 A | 4/1999 |
| JP | H11-258579 A | 9/1999 |
| JP | 2000-131676 A | 5/2000 |
| JP | 2003-107438 A | 4/2003 |
| JP | 2004-198505 A | 7/2004 |
| JP | 2004-280045 A | 10/2004 |
| JP | 2006-267562 A | 10/2006 |
| JP | 2006309185 A | 11/2006 |
| JP | 2007-065230 A | 3/2007 |
| JP | 2007094442 A | 4/2007 |
| JP | 2009025354 A1 | 2/2009 |
| JP | 2011-095407 A | 5/2011 |
| JP | 2011-515543 A | 5/2011 |
| JP | 2011-170278 A | 9/2011 |
| KR | 1993-0013794 A | 7/1993 |
| KR | 10-0163885 B1 * | 1/1999 |
| KR | 10-0244731 B1 | 2/2000 |
| KR | 10-0323004 B1 | 5/2002 |
| KR | 10-2005-0071661 A | 7/2005 |
| KR | 10-2005-0094011 A | 9/2005 |
| KR | 10-2006-0041921 A | 5/2006 |
| KR | 10-0752507 B1 | 8/2007 |
| KR | 10-2009-0105823 A | 10/2009 |
| KR | 10-2010-0050086 A | 5/2010 |
| KR | 10-1084675 B1 | 11/2011 |
| KR | 10-2012-0093231 A1 | 8/2012 |
| KR | 10-2012-0099183 A * | 9/2012 |
| KR | 10-2012-0125859 A | 11/2012 |
| TW | 386169 B | 4/2000 |
| TW | 200638087 A | 11/2006 |
| TW | 200837408 A | 9/2008 |
| TW | 201038719 A | 11/2010 |
| TW | 201127943 A1 | 8/2011 |
| WO | 2005/081051 A1 | 9/2005 |
| WO | 2011158569 A1 | 12/2011 |
| WO | 2012050177 A1 | 4/2012 |
| WO | WO2012050179 A1 | 4/2012 |

OTHER PUBLICATIONS

Office Action issued in Taiwanese Patent Application No. 102146520 dated Mar. 4, 2015 along with its English translation, 8 pages.
Search Report issued for European Patent Application No. 13863016.5 dated Jun. 14, 2016, 8 pages.
Hasebe H. et al., "Effect of Polymer Network Made of Liquid Crystalline Diacrylate on Characteristics of Liquid Crystal Display Device," Japanese Journal of Applied Physics, Japan Society of Applied Physics, JP, vol. 33, No. 11 (1994) pp. 6245-6248.
Database WPI Week 200943, Thomson Scientific, London, GB; AN 2009-J47017; XP002757789, 3 pages.
Office Action issued in Chinese Patent Application No. 201380073098.7 dated Mar. 25, 2016 along with its English translation, 16 pages.
Database WPI Week 201202 Thomson Scientific, London, GB; AN 2011-Q73804 XP02757909 (2 pages).
Office Action issued for Chinese Patent Application No. 201380072911.9 dated Mar. 2, 2017, 7 pages.
Office Action issued for Chinese Patent Application No. 201380073107.2 dated Mar. 1, 2017, 8 pages.

* cited by examiner

POLYMERIZABLE COMPOSITION AND METHOD FOR MANUFACTURING LIQUID CRYSTAL DEVICE

CROSS REFERENCE TO RELATED APPLICATIONS

This application is a 35 U.S.C. §371 National Phase Entry Application from PCT/KR2013/011681, filed Dec. 16, 2013, and designating the United States, which claims priority under 35 U.S.C. §119 to Korean Patent Application No. 10-2012-0146671 filed Dec. 14, 2012, to Korean Patent Application No. 10-2013-0156781 filed Dec. 16, 2013, to Korean Patent Application No. 10-2013-0156783 filed Dec. 16, 2013, and to Korean Patent Application No. 10-2013-0156785 filed Dec. 16, 2013, which are incorporated herein by reference in their entireties.

FIELD

The present application relates to a polymerizable composition, a method of manufacturing a liquid crystal device, and a system for manufacturing the liquid crystal device.

BACKGROUND

A liquid crystal display (LCD) embodies an image by orientationally ordering a nematic or smectic liquid crystal compound and switching an aligning property through voltage application. A process of manufacturing an LCD is a high-cost process requiring a complicated process, and needs a large-scale production line and equipment.

A so-called polymer dispersed liquid crystal (PDLC; the term "PDLC" used herein is a super ordinate concept including a so-called polymer network liquid crystal (PNLC) or polymer stabilized liquid crystal (PSLC)) device embodied by dispersing liquid crystals in a polymer matrix has been known. The PDLC can be manufactured through coating of a liquid crystal solution, and thus can be manufactured by a simpler process than that for a conventional LCD.

As described in the patent document 1, a normal liquid crystal compound is present while not aligned in a PDLC. Accordingly, the PDLC is opaque, which is a non-transparent state, when a voltage is not applied, and such a state is called a dispersing mode. When the voltage is applied to the PDLC, the liquid crystal compound is ordered according thereto to become a transparent state, and thus switching between transparent and dispersing modes is possibly performed.

PRIOR ART DOCUMENT

Patent Document (Patent Document 1) Korean Unexamined Patent Application Publication No. 1993-0013794

DETAILED DESCRIPTION

Object

The present application provides a polymerizable composition, a method of manufacturing a liquid crystal device, and a system for manufacturing the liquid crystal device.

Solution

One aspect of the present application provides a polymerizable composition, which may be used to form, for example, a liquid crystal layer of the following liquid crystal device. The liquid crystal layer of an illustrative liquid crystal device including the liquid crystal layer formed of the polymerizable composition may include an alignable polymer network and a liquid crystal compound. In one embodiment, the liquid crystal compound may be dispersed in the liquid crystal layer while being phase-separated from the alignable polymer network. The term "alignable polymer network" used herein refers to a polymer network formed to align a liquid crystal compound. The polymer network capable of aligning the liquid crystal compound may be formed by the following method. The liquid crystal compound which can be dispersed in the alignable polymer network may be orientationally ordered by an action of the alignable polymer network. In addition, an ordering direction of the liquid crystal compound orientationally ordered in one direction may be changed by an external action. The term "external action" used herein refers to all kinds of actions performed to change ordering of the liquid crystal compound, and a representative example thereof is the application of a voltage. The term "initial alignment or normal alignment" used herein may refer to an aligning or ordering direction of the liquid crystal compound or an optical axis of a liquid crystal layer formed by the liquid crystal compound in a state in which the external action is not present. In addition, the term "initial or normal state" used herein may refer to a state of the liquid crystal device without the external action. In the liquid crystal device, an ordering direction of the liquid crystal compound in the initial alignment state may be changed by an external action, and when the external action disappears, the liquid crystal compound may return to the initial alignment state.

The liquid crystal device may further include an alignment layer. The alignment layer may be, for example, disposed adjacent to the liquid crystal layer. The sentence "the alignment layer is disposed adjacent to the liquid crystal layer" means that the alignment layer is disposed to have an influence on the alignment of the liquid crystal layer, and in one embodiment, that the alignment layer is formed in contact with the liquid crystal layer. However, the alignment layer is not necessarily placed in contact with the liquid crystal layer as long as the alignment layer is placed to affect the alignment of the liquid crystal layer. FIG. 1 is a structure of an illustrative device, which includes an alignment layer 101 and a liquid crystal layer 102 formed on one surface of the alignment layer 101. The liquid crystal layer 102 is an example of a liquid crystal device including a polymer network 1021 and a liquid crystal region 1022. In FIG. 1, the alignment layer 101 is present only on one surface of the liquid crystal layer 102, but may be present on both surfaces of the liquid crystal layer. In the specification, the liquid crystal region may refer to a region in which the liquid crystal compound is present in the polymer network, and for example, as a region including the liquid crystal compound, refer to a region in which the liquid crystal compound is dispersed in the network while phase-separated from the polymer network. In FIG. 1, the liquid crystal compound in the liquid crystal region 1022 may be indicated with an arrow.

The liquid crystal device may include a polarizing layer disposed on one or both sides of the liquid crystal layer. As the polarizing layer, without particular limitation, a polarizing film formed of, for example, a conventional material used in a conventional LCD, such as poly(vinyl alcohol) (PVA), or a polarizing layer embodied by a coating method such as a polarized coating layer including a lyotropic liquid crystal (LLC), or a reactive mesogen (RM) and a dichroic dye. In the specification, the polarizing layer embodied by a coating method may be called a polarized coating layer. When the polarized coating layer includes an LLC, the coating layer may further include a protecting layer for protecting the LLC layer. As the LLC, without particular limitation, a known liquid crystal may be used, and for example, an LLC capable of forming an LLC layer having a dichroic ratio of approximately 30 to 40 may be used. Meanwhile, when the polarized coating layer includes an RM and a dichroic dye, a linear dye or a discotic dye may be used as a dichroic dye. When the polarizing layer is present, arrangement of a light absorption axis may be selected in consideration of, for example, normal alignment of the liquid crystal layer and a mode of the device, but the present application is not particularly limited thereto. For example, to embody a normally white-mode device, two polarizing layers are placed on both sides of the liquid crystal layer. Here, light absorption axes of the polarizing layers may be placed at any one angle within 80 to 100 degrees, for example, perpendicular to each other. In addition, for example, to embody a normally black mode, two polarizing layers are placed on both sides of the liquid crystal layer. Here, light absorption axes of polarizing layers may be disposed at any one angle within –10 to 10 degrees, for example, parallel to each other. In such a state, normal alignment of the liquid crystal layer may be placed at any one angle within 40 to 50 degrees, for example, at approximately 45 degrees with the light absorption axes of the two polarizing layers.

The liquid crystal device may include one or at least two base layers. Normally, the liquid crystal layer may be placed between the two base layers opposite to each other. In such a structure, the alignment layer may be disposed on an inner side of the base layer, for example, between the liquid crystal layer and the base layer. For example, the liquid crystal device may further include base layers opposite to each other, and the liquid crystal layer may be present between the base layers opposite to each other. In some cases, the alignment layer may be present between the liquid crystal layer and the base layer. FIG. 2 shows an illustrative liquid crystal device, which is present between base layers 201A and 201B spaced a predetermined distance apart from each other and opposite to each other, and includes an alignment layer 101 and a liquid crystal layer 102. When the base layer is present, the above-described polarizing layer may be normally present on an outer side of the base layer, but when needed, may be present on an inner side of the base layer, that is, between the liquid crystal layer and the base layer. In such a case, as the polarizing layer, it is preferable to use the above-described polarized coating layer.

As the base layer, a known material may be used without particular limitation. For example, an inorganic film such as a glass film, a crystalline or non-crystalline silicon film, or a quartz or indium tin oxide (ITO) film, or a plastic film may be used. As the base layer, an optically isotropic base layer, an optically anisotropic base layer or polarizing plate such as a retardation layer, or a color filter substrate may be used. For example, when the polarizing layer is present on the inner side of the base layer, that is, between the liquid crystal layer and the base layer, although an anisotropic base layer is used as the base layer, a device having a suitable performance can be embodied.

A plastic base layer may be, but is not limited to, a base layer including triacetyl cellulose (TAC); a cyclo olefin copolymer (COP) of a norbornene derivative; poly(methyl methacrylate (PMMA); polycarbonate (PC); polyethylene (PE); polypropylene (PP); polyvinyl alcohol (PVA); diacetyl cellulose (DAC); polyacrylate (Pac); poly ether sulfone (PES); polyetheretherketon (PEEK); polyphenylsulfone (PPS), polyetherimide (PEI); polyethylenemaphthatlate (PEN); polyethyleneterephtalate (PET); polyimide (PI); polysulfone (PSF); polyarylate (PAR), or an amorphous fluorine resin. In the base layer, as needed, a coating layer of a silicon compound such as gold, silver, silicon dioxide, or silicon monoxide, a coating layer such as an anti-reflective layer may be present.

An electrode layer may be included on a surface of the base layer, for example, a surface on the liquid crystal layer of the base layer (for example, the alignment layer 101 of FIG. 2) or a surface of the base layer 201A or 201B in contact with the liquid crystal layer 102. The electrode layer may be formed by depositing, for example, a conductive polymer, a conductive metal, a conductive nanowire, or a metal oxide such as ITO. The electrode layer may be formed to have transparency. In this field, various materials and methods for forming a transparent electrode layer are known, and all of these methods may be applied. When needed, the electrode layer formed on the surface of the base layer may be suitably patterned.

A liquid crystal compound in the liquid crystal layer may be present in a normal state, for example, in a state in which the compound is orientationally ordered without an external action such as application of a voltage, and such an ordering direction may be changed by an external action, for example, application of an external voltage. Accordingly, in the present application, a device which can be exchanged between white and black modes can be embodied. For example, the device of the present application is a device embodied in a white mode without an external action (that is, in an initial state or a normal state), converted into a black mode under an external action, and then converted into a white mode when an external action is removed (such a device may normally refer to a white-mode device for convenience), or a device embodied in a black mode without an external action (that is, an internal state or a normal state), converted into a white mode under an external action, and then converted in a black mode when an external action is removed (such a device may normally refer to a black-mode device for convenience). For example, as described above, a normally white-mode device can be embodied when a liquid crystal layer is normally disposed at any one angle within 40 to 50 degrees, for example, 45 degrees with a light absorption axis of the polarizing layer between two polarizing layers whose light absorption axes are disposed at any one angle within 80 to 100 degrees, for example, disposed perpendicular to each other. In another example, as described above, a normally black-mode device can be embodied when a liquid crystal layer is normally disposed at any one angle within 40 to 50 degrees, for example, 45 degrees, with a light absorption axis of the polarizing layer between two polarizing layers whose light absorption axes are disposed at any one angle within –10 to 10 degrees, for example, disposed parallel to each other. In this state, a black mode can be embodied by changing an alignment state of the liquid crystal compound into, for example, a vertical alignment state by the application of a voltage. The term "black mode" used herein is a concept differentiated from, so called, a dispersing mode, in a normal PDLC, and for example, a haze in the black mode is 10% or less, 8% or less, 6% or less, or 5% or less. In addition, a haze in a white mode of the device of the present application is also 10% or less, 8% or less, 6% or less, or 5% or less. The haze may be a percentage of a transmittance of diffusion light with respect to a transmittance of entire transmission light penetrating a measuring target. The haze may be evaluated using a hazemeter (NDH-5000SP). The haze may be evaluated in the following method using the hazemeter. That is, light is transmitted through the measuring target, and incident into an integrating sphere. In this process, light is separated into diffusion light (DT) and parallel light (PT) by the measuring target, and these lights are reflected in the integrating sphere, and then collected in a light-receiving device. The haze can be measured through the collected light. That is, total transmission light (TT) obtained by the above process may be a sum (DT+PT) of the diffusion light (DT) and the parallel light (PT), and the haze may be defined as a percentage (Haze(%)=100×DT/TT) of the diffusion light to the total transmission light. In addition, the liquid crystal device of the present application may exhibit excellent transparency in a transmission mode. For example, the liquid crystal device may exhibit light transmittance of 80% or more, 85% or more, 90% or more, or 95% or more without an external action in a normal alignment state, that is, a non-application of a voltage when the liquid crystal device is in a normal white mode. In addition, in a normal black mode, while an external action such as application of a voltage is present, the above-described light transmittance may be exhibited. The light transmittance may be a light transmittance with respect to any one wavelength in a visible region, for example, within approximately 400 to 700 nm.

The liquid crystal device may have a high contrast ratio. The term "contrast ratio" used herein may refer to a rate (T/B) of a brightness (T) in the white mode to a brightness (B) in a black mode. In one embodiment, the liquid crystal device includes the liquid crystal layer, and two polarizing layers, that is, first and second polarizing layers, disposed on both sides of the liquid crystal layer. The maximum value of the contrast ratio may be 200 or more, 250 or more, 300 or more, or 350 or more. It means that the higher the contrast ratio is, the higher performance the device has, and thus the upper limit of the contrast ratio is not particularly limited. For example, the contrast ratio may be 600, 550, 500, 450, or 400 or less. Such a contrast ratio may be performed by embodying the device using the above-described alignable polymer network and polarizing layer.

The liquid crystal device can be driven through low energy consumption, for example, a low driving voltage. For example, the liquid crystal device may have a voltage required to exhibit a 10% light transmittance or 90% light transmittance of 30 V or less, 25 V or less, or 20 V or less. That is, in the case of a normally white-mode device, a black mode can be embodied by changing an alignment direction of the liquid crystal compound by the application of a voltage, and in such a process, a voltage required to exhibit a light transmittance of 10% may be in the above range. In contrast, in the case of the normally-black mode device, a white mode can be embodied by changing an alignment direction of the liquid crystal compound by the application of a voltage, and in such a process, a voltage required to have a light transmittance of 90% may be in the above range. It means that the lower the voltage is, the higher performance the device has, and thus the lower limit of the required voltage is not particularly limited. For example, the required voltage may be 5 V or more. Such a low driving voltage may be obtained by embodying a device using the above-described alignable polymer network and polarizing layer.

The liquid crystal layer of the liquid crystal device includes a polymer network and a liquid crystal compound dispersed in the polymer network, and thus may have excellent thermal stability. For example, the liquid crystal layer may satisfy the following Equation A when maintained for 200 hours at 70° C. before and after thermal treatment.

$$|100 \times (X_2 - X_1)/X_1| \leq 10\%$$ [Equation A]

In Equation A, $X_1$ is a retardation of the liquid crystal layer before the thermal treatment, and $X_2$ is a retardation of the liquid crystal layer after the thermal treatment.

That is, the liquid crystal layer of the liquid crystal device may have an absolute value of a variation rate of the retardation before and after the thermal treatment of 10% or less. As the absolute value of such a variation rate is lower, the liquid crystal layer may have better thermal stability, and the lower limit of the absolute value of the variation rate is not particularly limited.

The polymer network may be a network of a precursor including, for example, a polymerizable compound. Accordingly, the polymer network may include the polymerizable compound in a polymerized state. As the polymerizable compound, a non-liquid crystal compound that does not exhibit crystallinity may be used. When needed, as the polymerizable compound, a liquid crystal compound may be used, but in this case, a double refraction of the following polymer network may be considered.

For an alignment property of the polymer network, a composition of the polymerizable compound forming the polymer network may be controlled. For example, the polymer network or the precursor may include at least one of a bifunctional acrylate compound, a multifunctional, for example, tri- or more functional, acrylate compound and a monofunctional acrylate compound. The polymer network may include the compound in a crosslinked or polymerized state. The term "acrylate compound" used herein refers to a compound including an acryloyl group or a methacryloyl group, and the compound including one functional group is a monofunctional acrylate compound, and the compound including at least two functional groups is a multifunctional acrylate compound. For convenience of differentiation, hereinafter, the compound including two functional groups refer to a bifunctional acrylate compound, and a multifunctional, for example, tri- or more functional, acrylate compound simply refers to a multifunctional acrylate compound. The multifunctional acrylate compound may include, for example, 3 to 8, 3 to 7, 3 to 6, 3 to 5, or 3 to 4 functional groups.

To embody a suitable alignable polymer network, the polymer network or a precursor thereof may include at least one compound of the bifunctional, multifunctional and monofunctional acrylate compounds to satisfy Equations 1 to 3.

$$A \geq 1.3 \times B$$ [Equation 1]

$$A \geq C$$ [Equation 2]

$$A \geq 0.6 \times (B+C)$$ [Equation 3]

In Equations 1 to 3, A, B and C are weight ratios between the compounds calculated by converting the sum of weights of the bifunctional acrylate compound, the multifunctional acrylate compound and the monofunctional acrylate compound, which are present in the precursor or polymer network, into 100. For example, when the precursor or polymer network includes only a bifunctional acrylate compound, in Equations 1 to 3, A is 100, B and C are respectively 0. In another example, when the precursor or polymer network only includes bifunctional and monofunctional acrylate compounds, in Equations 1 to 3, each of A and C is 50, and B is 0.

To ensure a suitable alignment property, for example, in Equation 1, a value (A−1.3B) obtained by subtracting 1.3×B from A may be approximately 0.5 to 100 or 1 to 100. In addition, to ensure a suitable alignment property, for example, in Equation 2, a value (A−C) obtained by subtracting C from A may be 0 to 100. In addition, to ensure a suitable alignment property, in Equation 3, a value (A−0.6(B+C)) obtained by subtracting 0.6×(B+C) from A may be 2 to 100, 3 to 100, or 4 to 100.

To ensure a suitable alignment property, the polymer network or a precursor thereof may include at least one compound of the bifunctional, multifunctional and monofunctional acrylate compounds to satisfy Equations 4 to 6.

A≥40  [Equation 4]

B≤30  [Equation 5]

C≤50  [Equation 6]

In Equations 4 to 6, A, B and C are as described in Equations 1 to 3.

In the above range, a suitable alignment property can be ensured in the polymer network.

A kind of the acrylate compound included in the polymer network or a precursor thereof is not particularly limited, and for example, any kind of the acrylate compound included in the polymer network or a precursor thereof, which can exhibit an aligning property within the range satisfying the above Equation, may not be used.

For example, as the bifunctional acrylate compound, a compound represented by the Formula 1 may be used.

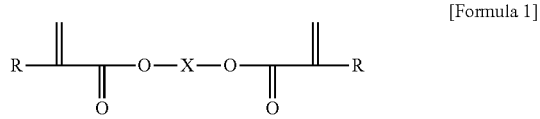

[Formula 1]

In Formula 1, R is each independently hydrogen or an alkyl group having 1 to 4 carbon atoms, and X is an alkylene or alkylidene group having 1 to 20 carbon atoms.

In addition, for example, as the multifunctional acrylate compound, a compound represented by Formula 2 may be used.

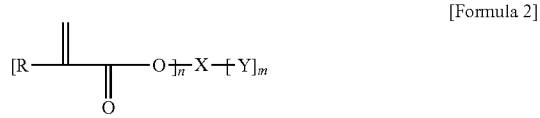

[Formula 2]

In Formula 2, n is a number of 3 or more, m is a number of 0 to 5, R is each independently hydrogen or an alkyl group having 1 to 4 carbon atoms, X is a (m+n) valent radical, and Y is hydrogen or an alkyl group.

In addition, for example, as the monofunctional acrylate compound, a compound represented by Formula 3 may be used.

[Formula 3]

In Formula 3, R is hydrogen or an alkyl group having 1 to 4 carbon atoms, and Z is an alkyl group having 1 to 20 carbon atoms.

In Formulas 1 to 3, as an example of the alkyl group capable of being present in R or Y, a methyl group or an ethyl group may be used.

In Formula 1, an alkylene group or alkylidene group of X may be, for example, an alkylene or alkylidene group having 1 to 16, 1 to 12, 1 to 10, 1 to 8, 2 to 8, or 4 to 8 carbon atoms. The alkylene or alkylidene group may be, for example, a linear, branched or cyclic type.

In Formula 2, n is any one of 3 or more, 3 to 8, 3 to 7, 3 to 6, 3 to 5, or 3 to 4. In addition, in Formula 2, m is any one of 0 to 5, 0 to 4, 0 to 3, 0 to 2, or 0 to 1.

In Formulas 2, X is a (m+n) valent radical, for example, a hydrocarbon having 2 to 20, 2 to 16, 2 to 12, 2 to 8, or 2 to 6 carbon atoms, for example, a (m+n) radical induced from a linear or branched alkane.

Meanwhile, in Formula 3, an alkyl group of X may be, for example, a linear or branched alkyl group having 1 to 20, 1 to 16, 1 to 12, 4 to 12, or 6 to 12 carbon atoms.

A substituent defined by Formulas 1 to 3, for example, an alkyl group, an alkylene group, an alkylidene group, or a (m+n) valent radical may be substituted by at least one substituent if needed, and as the substituent, for example, an alkyl group, an alkoxy group, an epoxy group, an oxo group, an oxetanyl group, a thiol group, a cyano group, a carboxyl group or an aryl group may be used, but the present application is not limited thereto.

The polymer network or a precursor thereof may further include an additive such as a solvent, a radical or cationic initiator capable of inducing polymerization of the polymerizable liquid crystal compound, a basic material, a reactive compound capable of forming a network, or a surfactant, when further needed in the above-described compound.

The polymer network or precursor thereof may include a liquid crystal compound, for example, a reactive liquid crystal compound. In such a case, a ratio of the liquid crystal compound is suitably controlled at a small amount. In one embodiment, the polymer network may have a double refraction of 30 nm or less or 20 nm or less. That is, the polymer network may be an isotonic polymer network or a network having a double refraction within the above range. Thus, when the liquid crystal compound is included, the polymer network may be included within a range exhibiting the above-described double refraction. The double refraction may refer to an in-plane retardation calculated by Equation 6, or a thickness-direction retardation calculated by Equation 7, and the lower limit may be 0 nm.

$$Rin = d \times (nx - ny)$$ [Equation 6]

$$Rth = d \times (nz - ny)$$ [Equation 7]

In Equations 6 and 7, Rin is an in-plane retardation, Rth is a thickness-direction retardation, d is a thickness of the polymer network, nx is a refractive index in a slow axis direction on a surface of the polymer network, ny is a refractive index in a fast axis direction on a surface of the polymer network, and nz is a refractive index of the polymer network in a thickness direction.

The polymer network and the liquid crystal compound in a liquid crystal region may satisfy Equation B.

$$(1-a) \times \{(2n_o^2 + n_e^2)/3\}^{0.5} \leq n_p \leq (1+a) \times n_e$$ [Equation B]

In Equation B, a is any one of 0 to 0.5, $n_o$ is an ordinary refractive index of the liquid crystal compound, $n_e$ is an extraordinary refractive index of the liquid crystal compound, and $n_p$ is a refractive index of the polymer network.

The term "refractive index, retardation or double refraction" used herein may be, unless particularly defined otherwise, a refractive index, retardation or double refraction measured with respect to light having a wavelength of 550 nm. In addition, when the ordinary refractive index of the polymer network is different from an extraordinary refractive index thereof, the term "refractive index of the polymer network" refers to an ordinary refractive index of the network. As the polymer network and the liquid crystal compound are selected to satisfy Equation B, a device exhibiting excellent transparency and ensuring a high contrast ratio in a white mode can be provided.

In Equation B, a may be, for example, less than 0.4, 0.3, 0.2, or 0.1, or 0.

The polymer network may have a dielectric anisotropy of 3 or more, 3.5 or more, or 4 or more. In such a range of the dielectric anisotropy, a driving voltage property of the liquid crystal device may be excellently maintained. The upper limit of the dielectric anisotropy may be, but is not particularly limited to, approximately 20 or less, 15 or less, or 10 or less.

A liquid crystal region dispersed in the polymer network includes a liquid crystal compound. As the liquid crystal compound, all kinds of compounds which are phase-separated in the polymer network, and aligned by the polymer network. For example, as the liquid crystal compound, a smectic liquid crystal compound, a nematic liquid crystal compound, or a cholesteric liquid crystal compound may be used. The liquid crystal compound may be phase-separated, may not be bound with the polymer network, and may be changed in an aligning property under an external action such as an external voltage. To this end, for example, the liquid crystal compound may be a compound without having a polymerizable group or crosslinking group.

In one embodiment, as the liquid crystal compound, a nematic liquid crystal compound may be used. As the compound, for example, as the liquid crystal compound satisfying Equation C, for example, a nematic liquid crystal compound may be used.

$$(n_e+n_o)/2-b \leq \{(2n_o^2+n_e^2)/3\}^{0.5} \leq (n_e+n_o)/2+b \quad \text{[Equation C]}$$

In Equation C, $n_e$ is an extraordinary refractive index of the liquid crystal compound, $n_o$ is an ordinary refractive index of the liquid crystal compound, and b is any one of 0.1 to 1.

As a liquid crystal compound satisfying Equation B is selected, a device exhibiting excellent transparency and ensuring high contrast ratio in a white mode can be provided.

In Equation 2, in another example, b is 0.1 to 0.9, 0.1 to 0.7, 0.1 to 0.5, or 0.1 to 0.3.

The liquid crystal compound may have a difference between an extraordinary dielectric anisotropy ($\in_e$, dielectric anisotropy in a longer axis direction) and an ordinary dielectric anisotropy ($\in_o$, dielectric anisotropy in a shorter axis direction) of 4 or more, 6 or more, 8 or more, or 10 or more. As the difference in dielectric anisotropy is higher, the device can exhibit suitable characteristics, and the upper limit is not particularly limited. For example, as the liquid crystal compound, a compound having an extraordinary dielectric anisotropy ($\in_e$, dielectric anisotropy in a longer axis direction) of approximately 6 to 50, and an ordinary dielectric anisotropy ($\in_o$, dielectric anisotropy in a shorter axis direction) of approximately 2.5 to 7.

A liquid crystal layer or the following polymerizable composition may include 5 to 50 parts by weight of the polymer network (or the following polymer network precursor) and 50 to 95 parts by weight of the liquid crystal compound. In another example, the liquid crystal layer or the following polymerizable composition may include 5 to 45 parts by weight of the polymer network (or the following polymer network precursor) and 55 to 95 parts by weight of the liquid crystal compound, 5 to 40 parts by weight of the polymer network (or the following polymer network precursor) and 60 to 95 parts by weight of the liquid crystal compound, 5 to 35 parts by weight of the polymer network (or the following polymer network precursor) and 65 to 95 parts by weight of the liquid crystal compound, 5 to 30 parts by weight of the polymer network (or the following polymer network precursor) and 70 to 95 parts by weight of the liquid crystal compound, 5 to 25 parts by weight of the polymer network (or the following polymer network precursor) and 75 to 95 parts by weight of the liquid crystal compound, 20 to 50 parts by weight of the polymer network (or the following polymer network precursor) and 80 to 95 parts by weight of the liquid crystal compound, or 5 to 15 parts by weight of the polymer network (or the following polymer network precursor) and 85 to 95 parts by weight of the liquid crystal compound. The term "pars by weight" used herein may refer to a weight ratio between components. Within such a range of the weight ratio, the aligning property of the polymer network may be suitably maintained.

A retardation (Rc) of the liquid crystal layer may be determined by a mode or structure of the device, but the present application is not particularly limited thereto. For example, the liquid crystal layer may have a retardation with respect to a wavelength of 550 nm of approximately 240 nm to 310 nm, 245 nm to 305 nm, or 250 nm to 300 nm Such a range of the retardation may be suitable to embody, for example, a normally white-mode device between two polarizing layers.

The liquid crystal layer may satisfy, for example, the following Equation D.

$$247 \text{ nm} \leq \{d \times (n_e - n_o)\} \times A \leq 302 \text{ nm} \quad \text{[Equation D]}$$

In Equation D, d is a thickness (unit: nm) of the liquid crystal layer, $n_e$ is an extraordinary refractive index of the liquid crystal compound, $n_o$ is an ordinary refractive index of the liquid crystal compound, and A is a ratio (L/T) of a weight (L) of the liquid crystal compound to a total weight (T) of the polymer network and the liquid crystal compound, or a ratio (VL/TV) of a volume (VL) of the liquid crystal compound to a total volume (TV) of the liquid crystal layer.

In Equation D, the value calculated by $\{d \times (n_e - n_o)\} \times A$ is a theoretical retardation of the liquid crystal layer. The theoretical retardation of the liquid crystal layer is suitable to approach a retardation (measured retardation) of the above-described liquid crystal layer. For example, in Equation D, an absolute value of a difference between the value calculated by $\{d \times (n_e - n_o)\} \times A$ and the measured retardation of the liquid crystal layer may be approximately 15 nm or less, 10 nm or less, 8 nm or less, or 5 nm or less. The liquid crystal layer satisfying Equation D may be suitable to embody, for example, a normally white-mode device between two polarizing layers.

In Equation D, $(n_e-n_o)$ may be, for example, 0.05 to 0.20. In another example, the $(n_e-n_o)$ may be 0.07 or more. In still another example, the $(n_e-n_o)$ may be 0.18 or less or 0.15 or less.

In Equation D, A is A is a ratio (L/T) of a weight (L) of the liquid crystal compound to a total weight (T) of the polymer network and the liquid crystal compound, or a ratio (VL/TV) of a volume (VL) of the liquid crystal compound to a total volume (TV) of the liquid crystal layer, which may be within 0.5 to 0.98. The ratio (L/T or VL/TV) may be, in another example, 0.6 or more or 0.7 or more.

A thickness of the liquid crystal layer is not particularly limited as long as it is set to satisfy the above description, and may be, for example, within approximately 1 μm to 10 μm.

When the liquid crystal device includes an alignment layer, as the alignment layer, for example, an alignment layer including a photo-alignment compound may be used. The term "photo-alignment compound" used herein may refer to a compound orientationally ordered through radiation of light, and capable of aligning an adjacent liquid crystal compound in a predetermined direction through an interaction such as anisotropic interaction in the ordered state. In the alignment layer, the photo-alignment compound may be ordered to have orientation. The photo-alignment compound may be a unimolecular compound, a monomeric compound, an oligomeric compound, or a polymeric compound.

A photo-alignment compound may be a compound including a photosensitive moiety. Various photo-alignment compounds capable of being used in alignment of the liquid crystal compound are known. As the photo-alignment compound, for example, a compound ordered by trans-cis photoisomerization; a compound ordered by photo-destruction such as chain scission or photo-oxidation; a compound ordered by photocrosslinking or photopolymerization such as [2+2] cycloaddition, [4+4] cycloaddition or photodimerization; a compound ordered by photo-Fries rearrangement; or a compound ordered by ring opening/closure. As the compound ordered by trans-cis photoisomerization, for example, an azo compound such as a sulfonated diazo dye or an azo polymer, or a stilbenes may be used, and as the compound ordered by photo-destruction, cyclobutane-1,2,3,4-tetracarboxylic dianhydride, aromatic polysilane or polyester, polystyrene or polyimide may be used. In addition, as the compound ordered by photocrosslinking or photopolymerization, a cinnamate compound, a coumarin compound, a cinnamamide compound, a tetrahydrophthalimide compound, a maleimide compound, a benzophenone compound or a diphenylacetylene compound or a compound having a chalconyl residue as a photosensitive residue (hereinafter, a chalcon compound) or a compound having an anthracenyl residue (hereinafter, an anthracenyl compound) may be used, as the compound ordered by photo-Fries rearrangement, an aromatic compound such as a benzoate compound, a benzoamide compound or a methacrylamidoaryl methacrylate compound may be used, and as the compound ordered by ring opening/closure, a compound ordered by ring opening/closure of a [4+2] π-electronic system such as a spiropyran compound may be used, but the present application is not limited thereto.

The photo-alignment compound may be a unimolecular compound, a monomeric compound, an oligomeric compound or a polymeric compound, or a blend of the photo-alignment compound and a polymer. Here, the oligomeric or polymeric compound may have a moiety induced from the photo-alignment compound or the photosensitive moiety at a main or side chain.

As the polymer having a moiety induced from the photo-alignment compound or the photosensitive moiety, and mixed with the photo-alignment compound, polynorbornene, polyolefin, polyarylate, polyacrylate, poly(meth)acrylate, polyimide, poly(amic acid), polymaleimide, polyacrylamide, polymethacrylamide, polyvinylether, polyvinylester, polystyrene, polysiloxane, polyacrylnitrile or polymethacrylnitrile may be used, but the present application is not limited thereto.

The polymer included in the alignment compound may be, but is not limited to, representatively, polynorbornene cinnamate, polynorbornene alkoxy cinnamate, polynorbornene allyloyloxy cinnamate, polynorbornene fluorinated cinnamate, polynorbornene chlorinated cinnamate, or polynorbornene dicinnamate.

When the alignment compound is a polymeric compound, the compound may have, but is not limited to, for example, a number average molecular weight of approximately 10,000 to 500,000 g/mol.

The alignment layer may be formed by, for example, blending a required additive such as a photoinitiator to the photo-aligned compound to coat, and radiating polarizing UV in a desired direction.

Another aspect of the present application provides a polymerizable composition. For example, the polymerizable composition may be used to form a liquid crystal layer of the above-described liquid crystal device. That is, the polymerizable composition may be a precursor composition of the liquid crystal layer.

For example, the polymerizable composition may include a precursor and a liquid crystal compound of an oriented polymer network including at least one of a bifunctional acrylate compound, a multifunctional, for example, tri- or more functional acrylate compound, and a monofunctional acrylate compound to satisfy Equations 1 to 3, if necessary, Equations 1 to 6.

In addition, for example, the polymerizable composition may include 50 to 95 parts by weight of the precursor and 5 to 50 parts by weight of the liquid crystal compound of the alignable polymer network including at least one of a bifunctional acrylate compound, a multifunctional, for example, tri- or more functional acrylate compound, and a monofunctional acrylate compound.

The illustrative polymerizable composition may include a precursor and a liquid crystal compound of an alignable polymer network. The precursor may be composed to form an alignable polymer network, for example, the above-described alignable polymer network. The precursor may include a polymerizable compound, for example, the bifunctional, multifunctional and/or monofunctional acrylate compound. The precursor may include the acrylate compound in a ratio satisfying the above-described Equations 1 to 6, and a kind or dielectric anisotropy of another acrylate compound, and the things relating to Equation B may also be applied in the same manner A kind of the liquid crystal compound included in the precursor is not particularly limited, either, and the above descriptions including, for example, the things relating to Equation C may be applied. In addition, the above description on the ratio of the precursor and the liquid crystal compound may also be applied.

The polymerizable composition may include a ball-shaped spacer in a suitable ratio to maintain the formed liquid crystal layer at a suitable distance, when needed. The shape and size of the spacer are not particularly limited, and may be selected to ensure a desired distance of the liquid crystal layer. The ratio of the spacer is not particularly limited, and may be included, for example, at approximately 0.1 wt % to 5 wt % in the total polymerizable composition.

The polymerizable composition may be prepared by dissolving an additive (for example, an initiator) additionally required to the precursor and the liquid crystal compound in a suitable solvent. As the solvent, known solvents such as toluene, xylene, cyclopentanone and cyclohexanone can be used.

In one embodiment, the polymerizable composition may be composed in a solventless type. The solvent-type polymerizable composition is preferable to be applied to the following squeeze coating method. A method of manufacturing the solventless-type poylmerizable composition is not particularly limited, and may control viscosities or ratios of other components without using the solvent which is included in the above-described composition.

Still another aspect of the present application provides a method of manufacturing a liquid crystal device. The manufacturing method may include forming a liquid crystal layer including a liquid crystal compound dispersed in a polymer network by polymerizing a layer formed by coating a polymerizable composition. Here, as the polymerizable composition, for example, a precursor composition of the above-described liquid crystal layer may be used. Here, the polymerization may be performed by radiating suitable energy, for example, light, capable of inducing polymerization.

A method of forming the layer including the polymerizable composition may be a known coating method such as roll coating, printing, inkjet coating, slit nuzzling, bar coating, comma coating, spin coating or gravure coating without particular limitation. In one embodiment, the layer including the polymerizable composition may be formed by a squeeze coating method. To apply a squeeze coating method, the above-described solventless-type composition may be used as the polymerizable composition. Through the application of a squeeze coating method, a more uniform liquid crystal layer can be formed, and the liquid crystal layer can be directly laminated with a base layer without a separate adhesive layer, which may be preferable for driving voltage.

In the squeeze coating method, the layer including the polymerizable composition may be formed by placing the polymerizable composition between two base layers, for example, between the above-described base layer, and applying a pressure to at least one of the base layer. Here, a method of applying the pressure may use a pressure roller without particular limitation. The application of the pressure may be performed simultaneously or sequentially to the entire surface of the base layer. FIG. 3 is a diagram showing the squeeze coating method. As shown in FIG. 3, first, a polymerizable composition 301, for example, the above-described solventless-type composition is placed on a predetermined part of a base layer 201A, and then a base layer 201B is placed thereon. Subsequently, a pressure roller 302 is placed on at least one of the base layers to sequentially press the base layer. Though not shown in FIG. 3, the above-described electrode layer and/or alignment layer may be disposed on an inner side of the base layers 201A and 201B, for example, on a side finally in contact with the liquid crystal layer. In the squeeze coating method, polymerization may be performed simultaneously with the pressing process, or performed after the pressing process.

To form a suitable oriented polymer network, the polymerization may be performed on the alignment layer. For example, the liquid crystal layer may be formed by forming the layer including the polymerizable composition, or forming the layer between two alignment layers opposite to each other and applying energy to polymerize.

The alignment layer may include, for example, a photo-aligned compound such as the above-described photo-aligned compound. Such an alignment layer may be formed by coating a precursor of the alignment layer on a suitable substrate, for example, the base layer, exposing the coated layer, and aligning the photo-aligned compound. FIG. 4 schematically shows a process of forming an alignment layer 101 by radiating light to the precursor of the alignment layer formed on a base layer 201A.

The precursor of the alignment layer may further include, for example, an initiator to the photo-aligned compound at an appropriate amount, and may also include another additive such as a surfactant when needed. The layer of the precursor of the alignment layer may be formed by coating the precursor by a conventional coating method such as bar coating, comma coating, inkjet coating or spin coating. For example, the above-described transparent electrode layer may be formed on a surface of the base layer on which the precursor layer is formed.

After the precursor layer is formed, energy may be applied by radiating light to the layer. The radiation of light may be performed after a solvent is volatilized by drying the formed layer under a suitable condition when the precursor includes a solvent. The drying may be performed, for example, for approximately 1 to 5 minutes at approximately 60 to 130° C., but the present application is not limited thereto.

The radiation of light may be performed to order the alignment compound including the precursor layer. Normally, the ordering of the alignment compound may be performed using linearly-polarized light. The wavelength or intensity of the radiated light may be selected to suitably order the alignment compound. The ordered photo-aligned compound is ordered by light in a visible or near-ultraviolet range, but when needed, light in a far-ultraviolet or near-infrared range may be used.

A layer including a polymerizable composition may be formed to be adjacent to the alignment layer by the above-described squeeze coating method after the alignment layer is formed. FIG. 5 schematically shows a process of forming a liquid crystal layer 102 by radiating light to a layer including a polymerizable composition present on a surface of the alignment layer 101 shown in FIG. 4. FIG. 5 shows that a liquid crystal layer is formed on one alignment layer, but when needed, the liquid crystal layer may be formed between two alignment layers as described above.

A polymer network and a liquid crystal region may be formed through polymerization of a polymer network precursor and phase separation of a liquid crystal compound according to the above-described process.

To form a suitable alignment network, the polymerization may be performed while the precursor layer for the liquid crystal layer, that is, the above-described layer including the polymerizable composition is maintained in a liquid crystal phase, for example, a nematic phase. When the layer is formed in a non-nematic state, for example, an isotropic phase, a suitable alignment property may not be ensured. To maintain the nematic phase, the polymerization may be performed at a temperature less than a nematic temperature (Tni) of the precursor layer for the liquid crystal layer, that is, the layer including the polymerizable composition. The term "nematic temperature" used herein refers to a temperature at which the layer is changed into an isotropic state from a nematic state, and the range of the temperature may be determined according to the composition of the layer. As long as the polymerization is performed at less than the nematic temperature of the layer, that is, while the layer is in a nematic state, the temperature is not particularly limited thereto.

Conditions for the application of energy for polymerization, for example, the radiation of light, are not particularly limited, as long as a polymer network is formed by polymerizing the polymerizable compound, and the liquid crystal compound is phase-separated to form the liquid crystal region. When needed, to further stimulate the formation of the polymer network, application of suitable heat or exposure may be performed before or after the radiation of light, or at the same time.

After the liquid crystal layer is formed through the above process, when needed, a process of disposing a polarizing layer on one or both sides of the liquid crystal layer may be further performed. For example, after the liquid crystal layer is formed, a process for disposing the polarizing layer on both sides of the liquid crystal layer such that light absorption axes have any one angle from 80 to 100 degrees, for example, are perpendicular to each other, or such that light absorption axes have any one angle from −10 to 10 degrees, for example, are parallel to each other may be further performed.

Yet another aspect of the present application provides a system for manufacturing a liquid crystal device, for example, the above-described liquid crystal device.

The manufacturing system may include a polymerization inducing means installed to provide energy capable of inducing polymerization of a precursor of the liquid crystal layer, for example, the above-described polymerizable composition. Here, detailed descriptions on a polymer network precursor included in the precursor of the liquid crystal layer and a liquid crystal compound may be the same as described above.

A kind of the polymerization inducing means is not particularly limited, and a heating or light radiating means may be used to apply or radiate energy such as heat or light to the precursor may be used.

The manufacturing system may also include a loading means installed to maintain the precursor layer for the liquid crystal layer. The liquid crystal layer can be formed through polymerization while the precursor layer is maintained by such a loading means.

A kind of the loading means is not particularly limited as long as it can load the precursor of the liquid crystal layer. For example, the loading means may be installed to maintain a surface of the precursor layer to be curved at least in the polymerization of the precursor of the liquid crystal layer. An example of such a loading means may be a roll.

That is, in one embodiment, the manufacturing system is, so called, a roll-to-roll manufacturing system, which includes at least one guide roll formed to transfer the precursor layer for the liquid crystal layer. Due to the guide roll, the layer can be transferred, and a liquid crystal device can be sequentially manufactured. In addition, the polymerization may progress on the guide roll while the surface of the layer is maintained in a curved form, and in this case, the guide roll may serve as the loading means. A more uniform liquid crystal layer can be formed by performing the polymerization while the surface of the liquid crystal layer is maintained in a curved form by the above-described guide roll. The roll-to-roll system may further include, for example, an unwinding roll releasing the layer or a base layer on which the layer will be formed and introducing towards the polymerization inducing means, or a winding roll winding the liquid crystal device whose manufacturing process such as polymerization is done to recover.

The manufacturing device may include a temperature control means installed to maintain a temperature for the polymerizable compound to be maintained in a liquid crystal phase like the above-described nematic phase at least during the polymerization, that is, while the polymerizable compound is polymerized.

The temperature control means is not particularly limited as long as it can be formed to maintain a suitable temperature, and may be composed of, for example, a temperature control drum and/or an inert gas purging chamber.

For example, if the manufacturing system is the above-described roll-to-roll system, as a temperature control drum, for example, a cooling drum, is included in the guide roll also capable of serving as the loading means to maintain a temperature in a suitable range during the polymerization. When needed, the system may be composed to be included in the inert gas purging chamber such as a region in which polymerization occurs while loaded to such a guide roll, and to include a polymerization inducing means in the purging chamber.

FIG. 6 is an illustrative diagram showing a predetermined part of the manufacturing system embodied as described above. The system includes a guide roll A including a temperature control means such as a cooling drum; and an inert gas purging chamber B installed to introduce the precursor layer C for the liquid crystal layer transferred by the guide roll A. In FIG. 6, the system includes the guide roll A including a temperature control means and having a chamber B, but may omit any one of the above two components as long as it maintains a suitable temperature. In such a configuration, a polymerization inducing means, for example, a UV lamp as show in FIG. 6, installed to apply energy onto the precursor layer transferred by the guide roll A may be further included, and may be present, for example, in the chamber B.

In the manufacturing device, specific kinds of other means except the above-described components are not particularly limited. For example, in the corresponding field, various methods embodying the roll-to-roll system are known, and such a method may be applied to the system by suitably being changed when needed.

For example, the roll-to-roll system may be configured by sequentially forming an electrode layer, forming an alignment layer, forming a layer including a polymerizable composition (for example, the layer of the polymerizable composition may be formed by the squeeze coating method) and polymerizing the layer, while transferring a base layer input by a conventional input means such as a unwinding roll (the base layer 201A in FIGS. 2 and 3) by at least one guide roll, to recover a product finally manufactured through a process of laminating or forming a polarizing layer by a recovering means such as winding roll when needed.

Yet another aspect of the present application provides a use of the liquid crystal device. The illustrative liquid crystal device may be simply and continuously manufactured through, for example, a roll-to-roll process. The liquid crystal device may also be embodied as a flexible device, and ensure excellent an excellent contrast ratio.

For example, the present application relates to an optical modulator including the liquid crystal device. As the optical modulator, a smart window, a window protecting film, a flexible display device, an active retarder for displaying 3D images or a viewing angle control film may be used, but the present application is not limited thereto. A method of configuring such an optical modulator is not particularly limited, and a conventional method may be applied as long as the liquid crystal device is used.

Effect

A liquid crystal device of the present application is a device capable of exhibiting a normally white mode or normally black mode, which can be driven with a low driving voltage by exhibiting a high contrast ratio, and exhibit excellent durability such as thermal stability. Such a liquid crystal device can be applied to various optical modulators such as a smart window, a window protecting film, a flexible display device, an active retarder for a 3D image display or a viewing angle control film.

EXPLANATION OF THE MARKS IN THE DRAWINGS

101: the alignment layer
102: the liquid crystal layer
1021: the polymer network
1022: the liquid crystal region
201A, 201B: base layers
301: the polymerizable composition
302: the pressure roller

ILLUSTRATIVE EMBODIMENTS

Hereinafter, the above will be described in more detail by Examples and Comparative Examples; however the scope of the above is not limited to the below.

EXAMPLE 1

Formation of Alignment Layer

A precursor of an alignment layer was prepared by dissolving a mixture of polynorbornene (PNBCi, molecular weight (Mw): 85,000, polydispersity index (PDI): approximately 4.75) including the repeating unit of Formula A and a photoinitiator (Irgacure 907) as an alignment compound in a toluene solvent to have a solid content of the polynorbornene of 2 wt %. An alignment layer was formed by coating the precursor of the alignment layer on a transparent electrode layer of a polycarbonate (PC) film on which an indium tin oxide (ITO) transparent electrode layer is formed, and applying linearly-polarized UV rays (1,200 mJ/cm$^2$) by means of a wire grid polarizer (WGP).

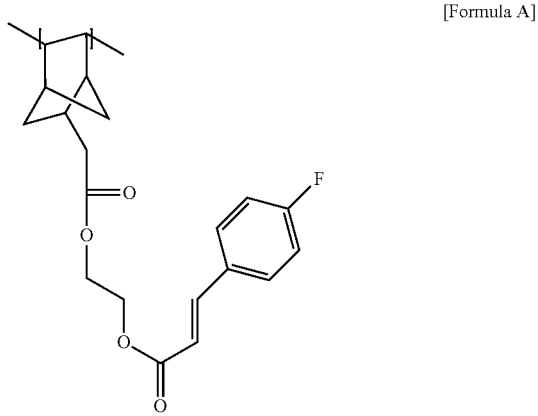

[Formula A]

Manufacture of Liquid Crystal Device

Figure 1:
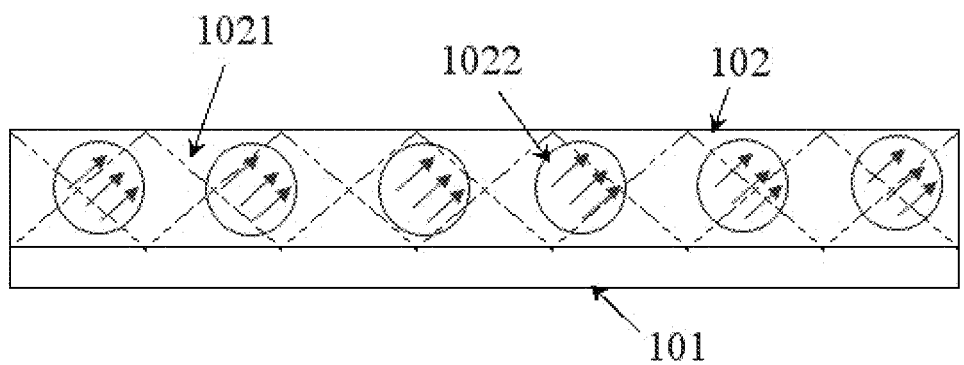
FIGS. 1 and 2 show an illustrative liquid crystal device.
Figure 2:
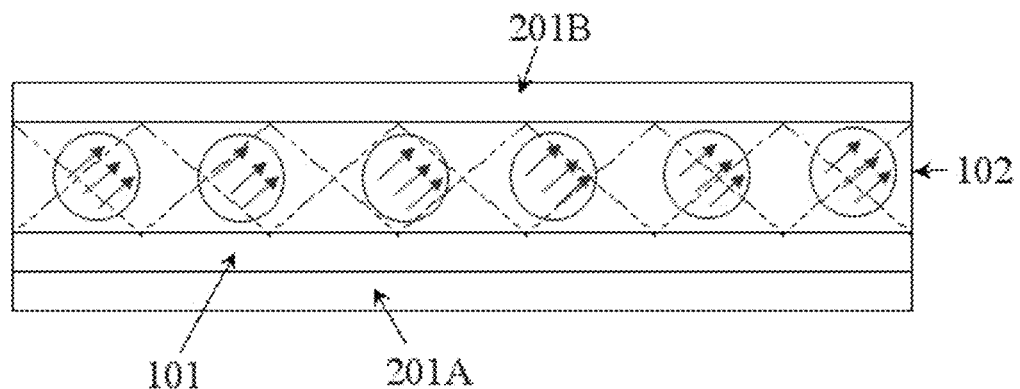
Figure 3:
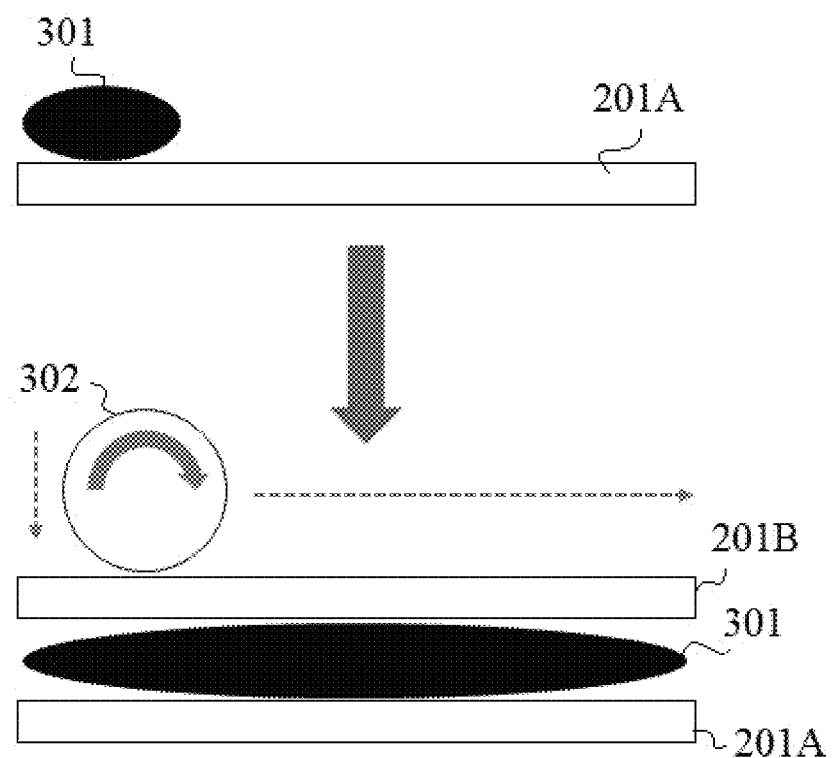
FIGS. 3 to 5 are diagrams illustrating a process of manufacturing the illustrative device.
Figure 4:
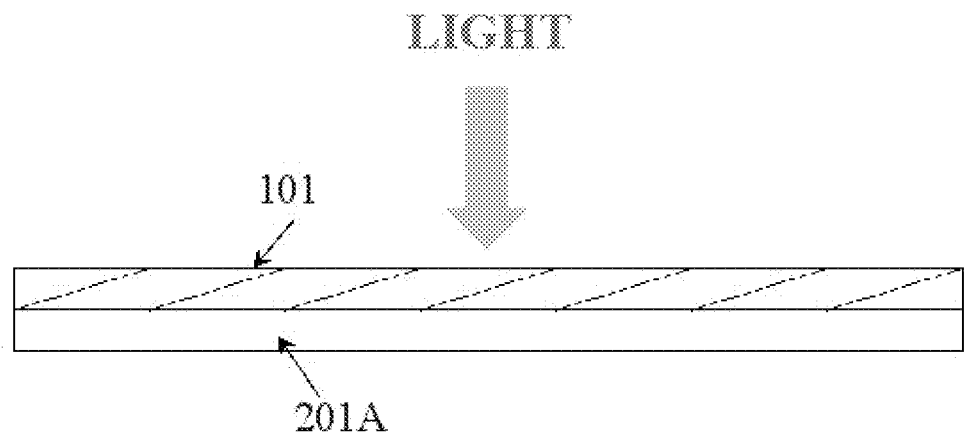
Figure 5:
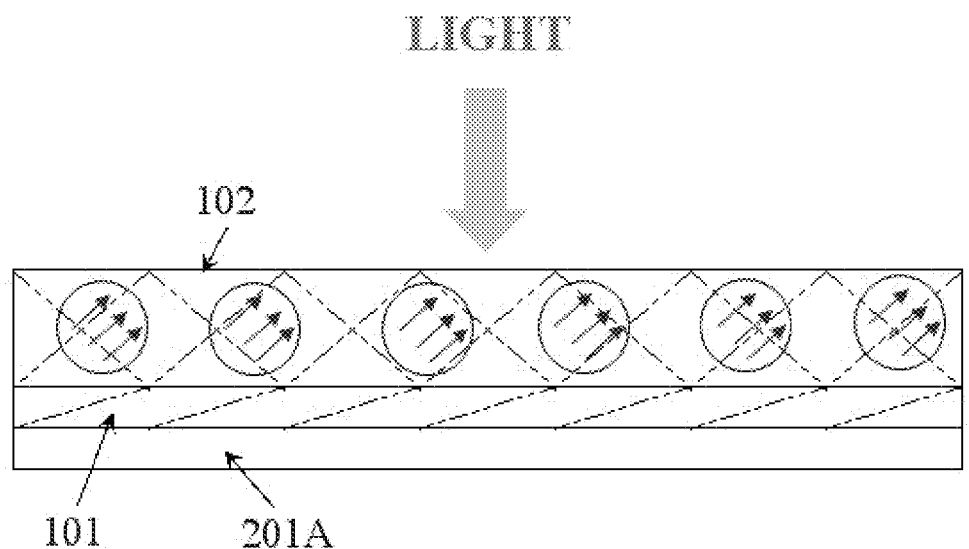
Figure 6:
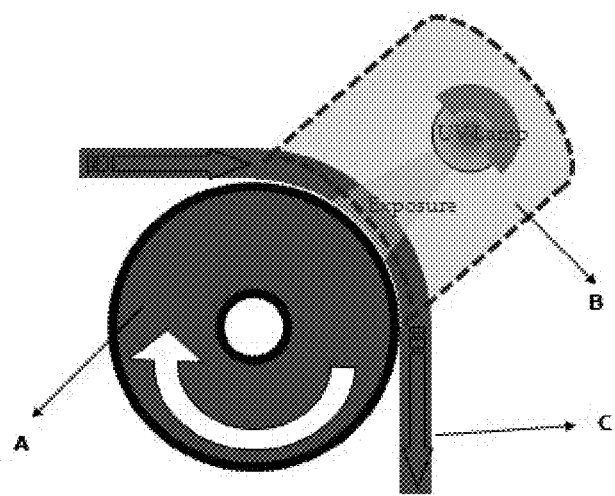
FIG. 6 is a diagram showing a system for manufacturing the illustrative liquid crystal device.
Figure 7:
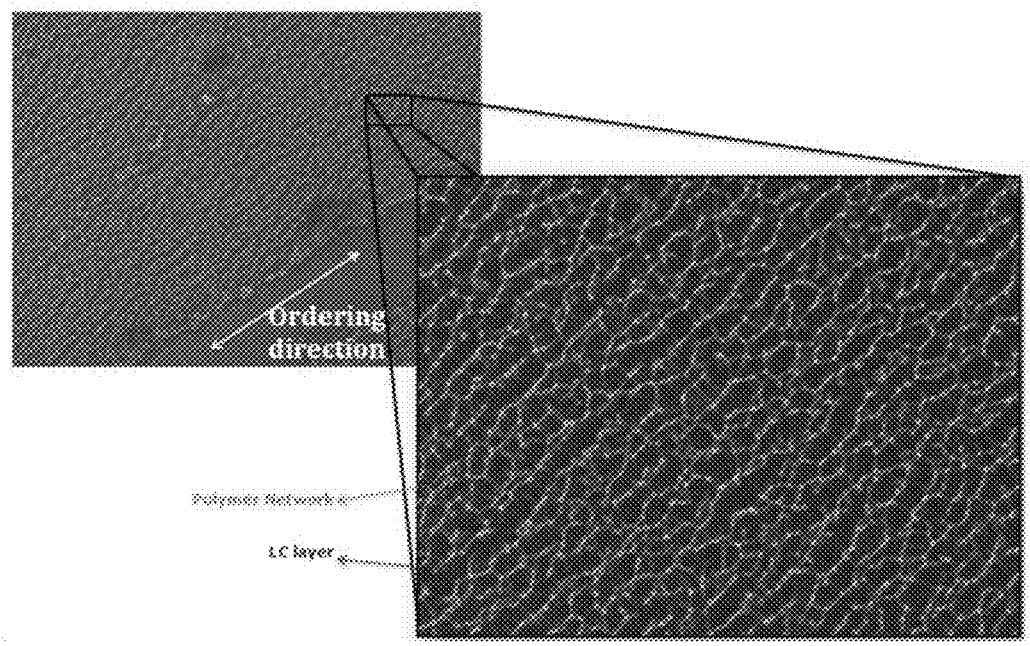
FIGS. 7 to 17 show evaluation results for the liquid crystal device in Examples and Comparative Examples.
Figure 8:
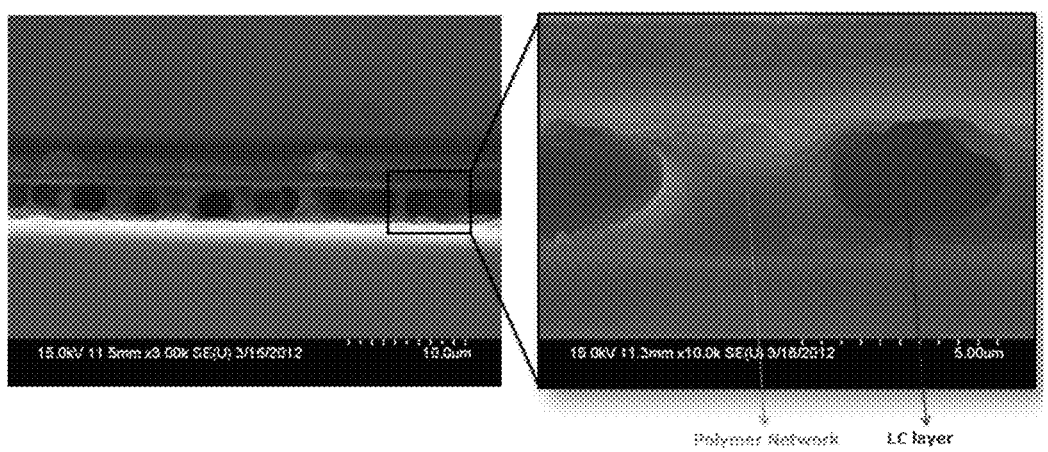

A precursor of a liquid crystal layer (polymerizable composition; nematic temperature (Tni): approximately 50° C.) was prepared by mixing 1.6-hexanediol diacrylate as a polymer network precursor with a liquid crystal compound (Merck, MAT-12-529, ne: 1.6092, no: 1.4820) in a weight ratio (polymer network precursor:liquid crystal compound) of 1:9, and dissolving the mixture in toluene with a suitable amount of an initiator. Afterward, the precursor of the liquid crystal layer was coated on a surface of the manufacture alignment layer to have a thickness of a final liquid crystal layer of 2.5 μm. A liquid crystal layer was formed by stacking a surface of the alignment layer of the PC film on one surface of which the alignment layer was formed to be in contact with the coating layer on the coated precursor of the liquid crystal layer, and polymerizing a polymer network precursor by radiating UV rays (300 mW/cm$^2$). A temperature during the UV radiation was maintained at approximately 25° C., and thus the precursor of the liquid crystal layer was maintained in a nematic phase. A refractive index of a polymer network for forming the liquid crystal layer measured with a prism coupler was approximately 1.456, and a phase retardation (measured retardation) of the liquid crystal layer was approximately 288 nm, which was measured using Axostep (Axometrics) equipment according to the manual of a manufacturer based on a wavelength of 550 nm. FIG. 7 is an optical microscope image of the liquid crystal layer, and FIG. 8 is a scanning electron microscope (SEM) image of the liquid crystal layer.

EXAMPLE 2

A liquid crystal layer was formed by the same method as described in Example 1, except that a mixture of 50 parts by weight of 1,6-hexanediol diacrylate and 50 parts by weight of 2-ethylhexyl acrylate was used as a polymer network precursor. Here, a nematic temperature (Tni) of the precursor of the liquid crystal layer was approximately 45° C., and the UV radiation was performed at a temperature maintaining the precursor in a nematic phase, for example, 25° C. A refractive index of the polymer network in the formed liquid crystal layer was approximately 1.446, and the measured retardation of the liquid crystal layer was approximately 286.7 mm.

EXAMPLE 3

A liquid crystal layer was formed by the same method as described in Example 1, except that a mixture of 40 parts by weight of 1,6-hexanediol diacrylate, 20 parts by weight of trimethylolpropane triacrylate and 40 parts by weight of 2-ethylhexyl acrylate was used as a polymer network precursor. Here, a nematic temperature (Tni) of the precursor of the liquid crystal layer was approximately 45° C., and the UV radiation was performed at a temperature maintaining the precursor in a nematic phase, for example, 25° C. A refractive index of the polymer network in the formed liquid crystal layer was approximately 1.452, and the measured retardation of the liquid crystal layer was approximately 285.3 mm.

EXAMPLE 4

A liquid crystal layer was formed by the same method as described in Example 1, except that a mixture of 40 parts by weight of 1,6-hexanediol diacrylate, 30 parts by weight of trimethylolpropane triacrylate and 30 parts by weight of 2-ethylhexyl acrylate was used as a polymer network precursor. Here, a nematic temperature (Tni) of the precursor of the liquid crystal layer was approximately 50° C., and the UV radiation was performed at a temperature maintaining the precursor in a nematic phase, for example, 25° C. A refractive index of the polymer network in the formed liquid crystal layer was approximately 1.455, and the measured retardation of the liquid crystal layer was approximately 286.1 mm.

EXAMPLE 5

A liquid crystal layer was formed by the same method as described in Example 1, except that a mixture of 70 parts by weight of 1,6-hexanediol diacrylate and 30 parts by weight of trimethylolpropane triacrylate was used as a polymer network precursor. Here, a nematic temperature (Tni) of the precursor of the liquid crystal layer was approximately 50° C., and the UV radiation was performed at a temperature maintaining the precursor in a nematic phase, for example, 25° C. A refractive index of the polymer network in the formed liquid crystal layer was approximately 1.461, and the measured retardation of the liquid crystal layer was approximately 287 mm.

COMPARATIVE EXAMPLE 1

A liquid crystal layer was formed by the same method as described in Example 1, except that a mixture of 40 parts by weight of 1,6-hexanediol diacrylate, and 60 parts by weight of 2-ethylhexyl acrylate was used as a polymer network precursor, and the polymer network precursor and the liquid crystal compound were mixed in a weight ratio (polymer network precursor:liquid crystal compound) of 10:90. Here, a nematic temperature (Tni) of the precursor of the liquid crystal layer was approximately 45° C., and the UV radiation was performed at a temperature maintaining the precursor in a nematic phase, for example, 25° C. A refractive index of the polymer network in the formed liquid crystal layer was approximately 1.444, and the measured retardation of the liquid crystal layer was approximately 124 mm.

COMPARATIVE EXAMPLE 2

A liquid crystal layer was formed by the same method as described in Example 1, except that a mixture of 30 parts by weight of 1,6-hexanediol diacrylate, 20 parts by weight of trimethylolpropane triacrylate and 50 parts by weight of 2-ethylhexyl acrylate was used as a polymer network precursor, and the polymer network precursor and the liquid crystal compound were mixed in a weight ratio (polymer network precursor:liquid crystal compound) of 10:90. Here, a nematic temperature (Tni) of the precursor of the liquid crystal layer was approximately 45° C., and the UV radiation was performed at a temperature maintaining the precursor in a nematic phase, for example, 25° C. A refractive index of the polymer network in the formed liquid crystal layer was approximately 1.450, and the measured retardation of the liquid crystal layer was approximately 162 mm.

COMPARATIVE EXAMPLE 3

A liquid crystal layer was formed by the same method as described in Example 1, except that a mixture of 30 parts by weight of 1,6-hexanediol diacrylate, 40 parts by weight of trimethylolpropane triacrylate and 30 parts by weight of 2-ethylhexyl acrylate was used as a polymer network precursor, and the polymer network precursor and the liquid crystal compound were mixed in a weight ratio (polymer network precursor:liquid crystal compound) of 10:90. Here, a nematic temperature (Tni) of the precursor of the liquid crystal layer was approximately 45° C., and the UV radiation was performed at a temperature maintaining the precursor in a nematic phase, for example, 25° C. A refractive index of the polymer network in the formed liquid crystal layer was approximately 1.457, and the measured retardation of the liquid crystal layer was approximately 166 mm.

COMPARATIVE EXAMPLE 4

A liquid crystal layer was formed by the same method as described in Example 1, except that a mixture of 40 parts by weight of 1,6-hexanediol diacrylate, 40 parts by weight of trimethylolpropane triacrylate and 20 parts by weight of 2-ethylhexyl acrylate was used as a polymer network precursor, and the polymer network precursor and the liquid crystal compound were mixed in a weight ratio (polymer network precursor:liquid crystal compound) of 10:90. Here, a nematic temperature (Tni) of the precursor of the liquid crystal layer was approximately 50° C., and the UV radiation was performed at a temperature maintaining the precursor in a nematic phase, for example, 25° C. A refractive index of the polymer network in the formed liquid crystal layer was approximately 1.459, and the measured retardation of the liquid crystal layer was approximately 157 mm.

COMPARATIVE EXAMPLE 5

A liquid crystal layer was formed by the same method as described in Example 1, except that a mixture of 60 parts by weight of 1,6-hexanediol diacrylate and 40 parts by weight of trimethylolpropane triacrylate was used as a polymer network precursor, and the polymer network precursor and the liquid crystal compound were mixed in a weight ratio (polymer network precursor:liquid crystal compound) of 10:90. Here, a nematic temperature (Tni) of the precursor of the liquid crystal layer was approximately 50° C., and the UV radiation was performed at a temperature maintaining the precursor in a nematic phase, for example, 25° C. A refractive index of the polymer network in the formed liquid crystal layer was approximately 1.463 and the measured retardation of the liquid crystal layer was approximately 182 mm.

COMPARATIVE EXAMPLE 6

A liquid crystal layer was formed by the same method as described in Example 1, except that only a liquid crystal compound was injected between PC films having an alignment layer to form a liquid crystal layer without using a polymer network precursor. Here, a measured retardation of the liquid crystal layer was approximately 319 nm.

COMPARATIVE EXAMPLE 7

A liquid crystal layer switched between a dispersing mode and a transparent mode was formed by forming a liquid crystal layer having a thickness of approximately 25 μm between two PC films not having an alignment layer using a precursor of a liquid crystal layer prepared by mixing 40 parts by weight of a polymer network precursor (PN-393, Merck) and 60 parts by weight of a liquid crystal compound as a precursor capable of forming a device switched between a dispersing mode and a transparent mode. A haze in the dispersing mode of the layer crystal layer formed as described above was approximately 92.91%, and a retardation thereof was approximately 65 nm.

COMPARATIVE EXAMPLE 8

A liquid crystal layer was formed by the same method as described in Example 1, except that a precursor of a liquid crystal layer prepared by mixing 10 parts by weight of a reactive liquid crystal compound and 90 parts by weight of a liquid crystal compound using a reactive liquid crystal compound (RM257, Merck) as a polymer network precursor was used. Here, a nematic temperature of the precursor of the liquid crystal layer was approximately 85° C., and the UV radiation was performed at a temperature maintaining the precursor in a nematic phase, for example, 25° C.

COMPARATIVE EXAMPLE 9

A liquid crystal layer was formed by the same method as described in Example 1, except that a mixture of 20 parts by weight of 1,6-hexanediol diacrylate and 80 parts by weight of a liquid crystal compound was used as a polymer network precursor. Here, a nematic temperature (Tni) of the precursor of the liquid crystal layer was approximately 10° C., and the UV radiation was performed at a temperature in which the precursor was maintained in an isotropic phase, for example, 25° C. A retardation (measured retardation) of the liquid crystal layer measured using Axostep (Axometrics) equipment according to the manual of a manufacturer based on a wavelength of 550 nm was approximately 139 nm.

COMPARATIVE EXAMPLE 10

A liquid crystal layer was formed by the same method as described in Example 1, except that UV radiation was performed at a temperature in which a precursor of a liquid crystal layer was maintained in an isotropic phase, for example, 60° C. Here, a refractive index of a polymer network in the manufactured liquid crystal layer measured using a prism coupler was approximately 1.456, and a retardation (measured retardation) of the liquid crystal layer measured using Axostep (Axometrics) equipment according to the manual of a manufacturer based on a wavelength of 550 nm was approximately 88 nm FIG. 18 shows data of the liquid crystal layer, which was measured by Axostep.

COMPARATIVE EXAMPLE 11

A liquid crystal layer was formed by the same method as described in Example 1, except that a PC film not having a photo-alignment layer was used. Here, a refractive index of a polymer network in the manufactured liquid crystal layer measured using a prism coupler was approximately 1.456, and a retardation (measured retardation) of the liquid crystal layer measured using Axostep (Axometrics) equipment according to the manual of a manufacturer based on a wavelength of 550 nm was approximately 46 nm FIG. 18 shows data of the liquid crystal layer, which was measured by Axostep.

COMPARATIVE EXAMPLE 12

A liquid crystal layer was formed by the same method as described in Example 1, except that a precursor of a liquid crystal layer was prepared by blending a polymer network precursor and a liquid crystal compound in a weight ratio (polymer network precursor:liquid crystal compound) of 4:6. A retardation (measured retardation) of the liquid crystal layer measured using Axostep (Axometrics) equipment according to the manual of a manufacturer based on a wavelength of 550 nm was approximately 139 nm.

EXPERIMENTAL EXAMPLE 1

Evaluation of Alignment Property of Polymer Network

Figure 9:
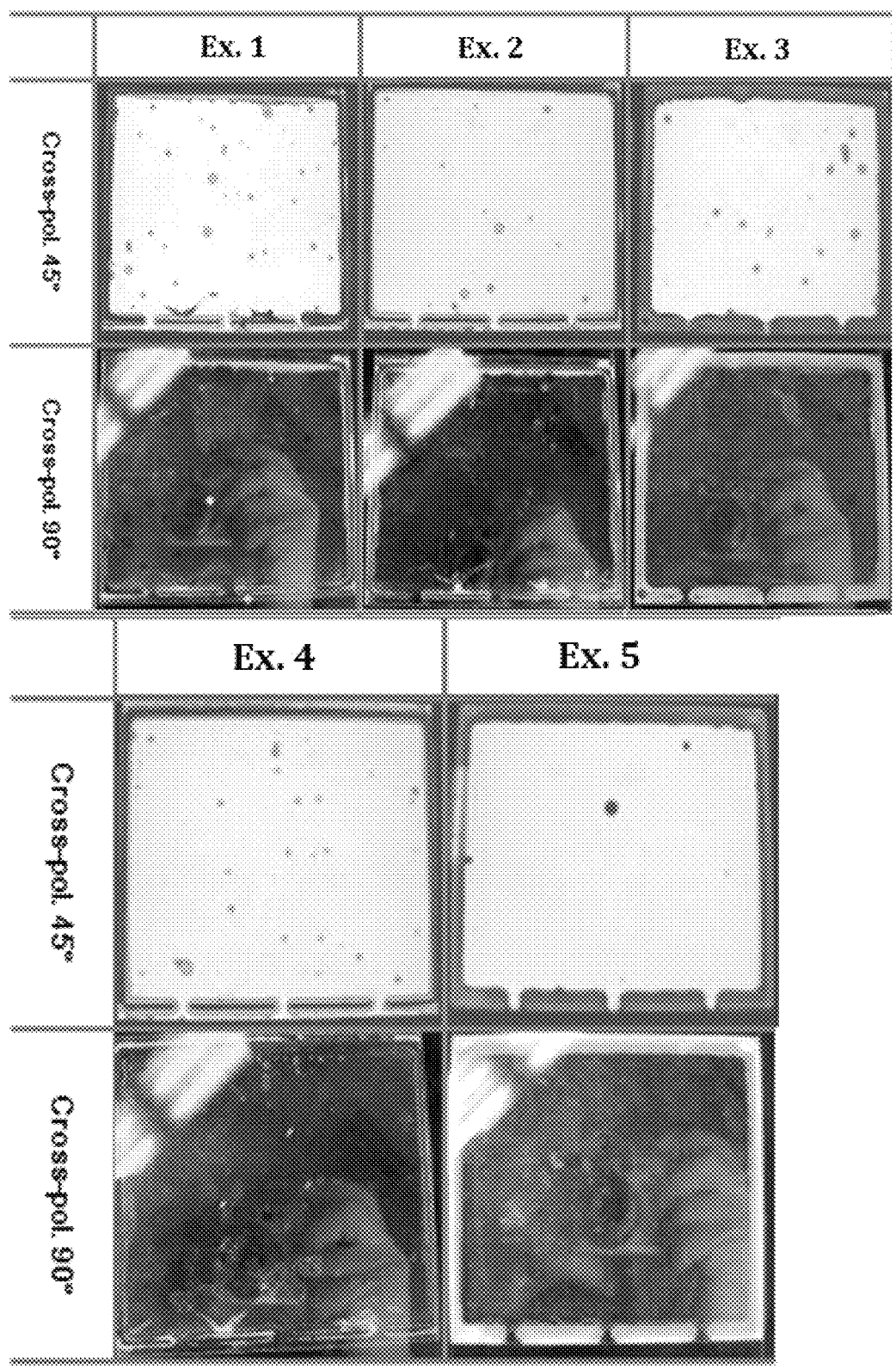
Figure 10:
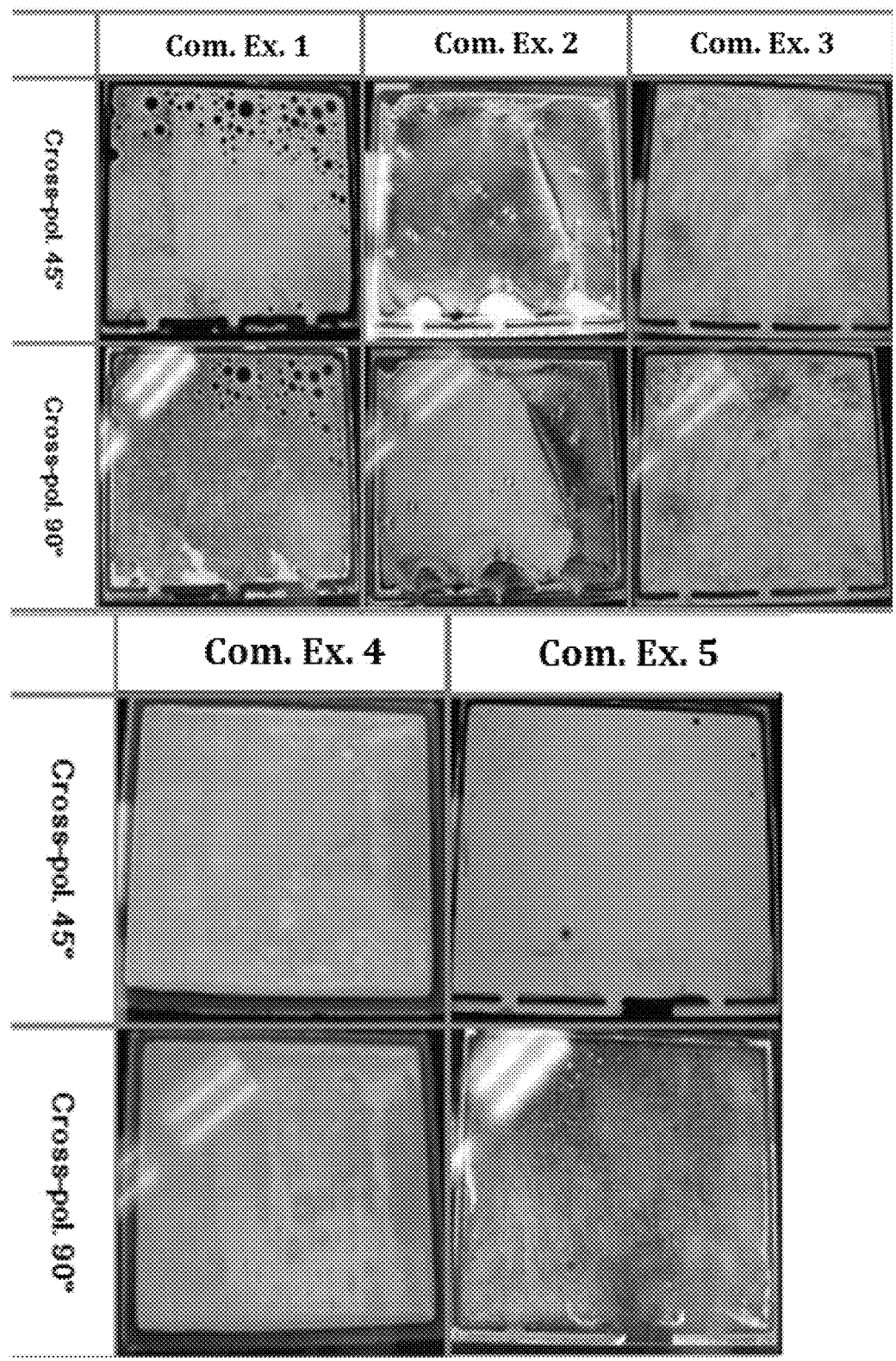
Figure 16:
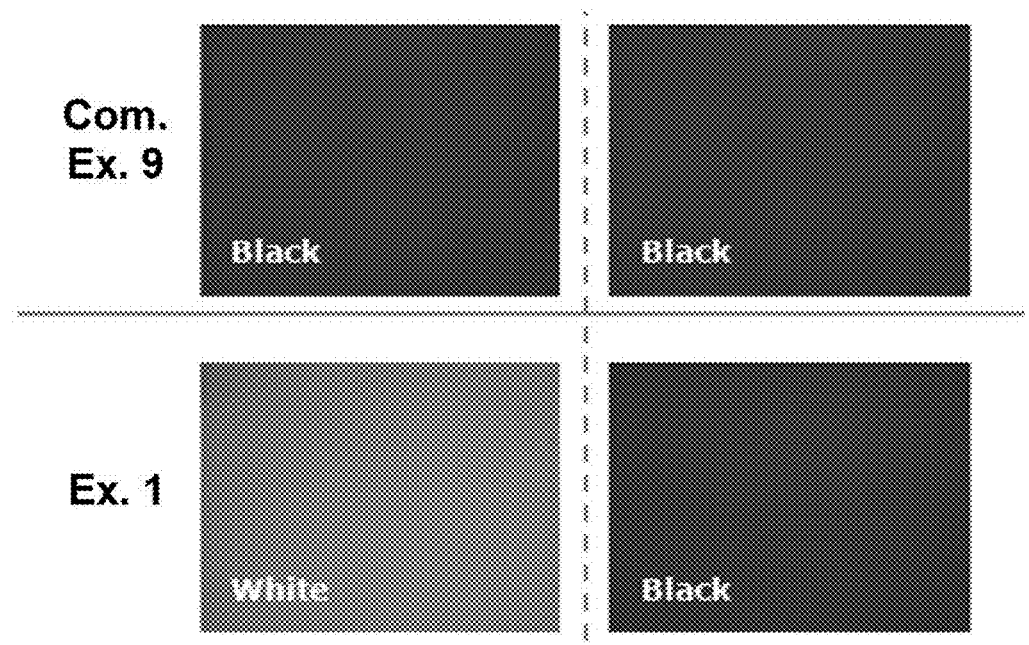
Figure 17:
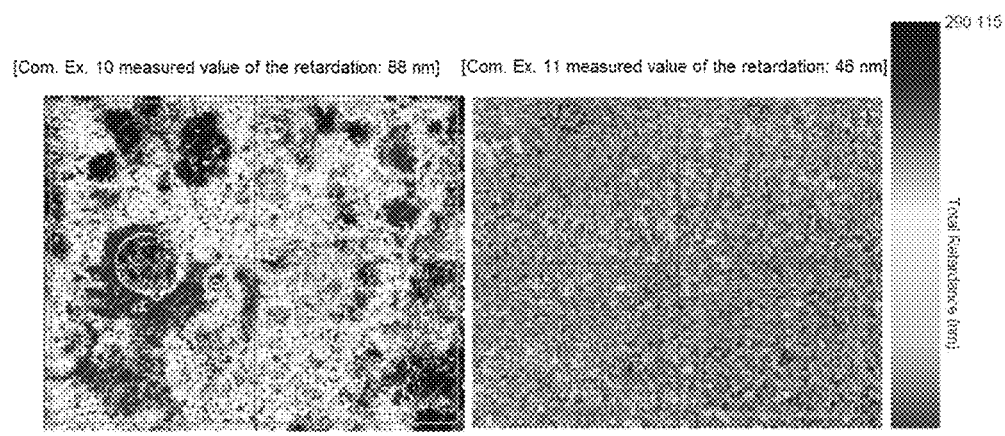

The liquid crystal layer manufactured in Example was placed between two polarizing plates disposed such that light absorption axes were perpendicular to each other or between two polarizing plates in which light absorption axes were disposed at 45 degrees, and an alignment property was evaluated by confirming whether the liquid crystal layer was switched between a white mode and a black mode while revolving. When the liquid crystal layer was switched between the white and black modes through the above-described process, it was evaluated that a liquid crystal compound was aligned in the liquid crystal layer due to the alignment property of a polymer network. According to the evaluation results, in Examples 1 to 5, switching between the white and black modes was confirmed, but in Comparative Examples 1 to 5 and Comparative Examples 9 to 12, polymer networks did not exhibit alignment properties. FIG. 9 shows evaluation results with respect to Comparative Examples 1 to 5, and FIG. 10 shows evaluation results with respect to Comparative Examples 1 to 5. In addition, FIG. 16 is a diagram showing the comparison between Example 1 and Comparative Example 9, and in Example 1 in which the formation of the liquid crystal layer was performed in a nematic phase of a precursor as confirmed from the drawings, a white mode (left) was exhibited when the liquid crystal layer was disposed at 45 degrees with a polarization axis, and a black mode (right) was exhibited when the liquid crystal layer was disposed at 90 degrees with a polarization axis. However, in Comparative Example 9 in which the formation of a liquid crystal layer was performed in a state in which a precursor was in an isotropic state, it was seen that switching between the white and black modes was impossible since light was blocked at both states in which the liquid crystal layer was disposed at 45 and 90 degrees (left and right) with the polarization axis.

EXPERIMENTAL EXAMPLE 2

Evaluation of Retardation, Haze and Transmittance of Liquid Crystal Layer

Figure 11:
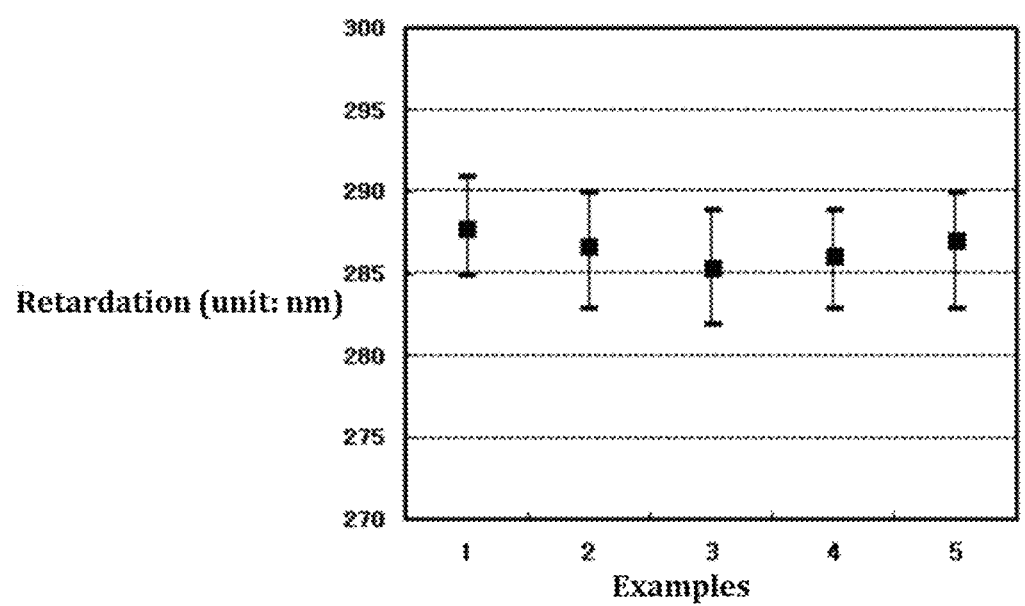
Figure 12:
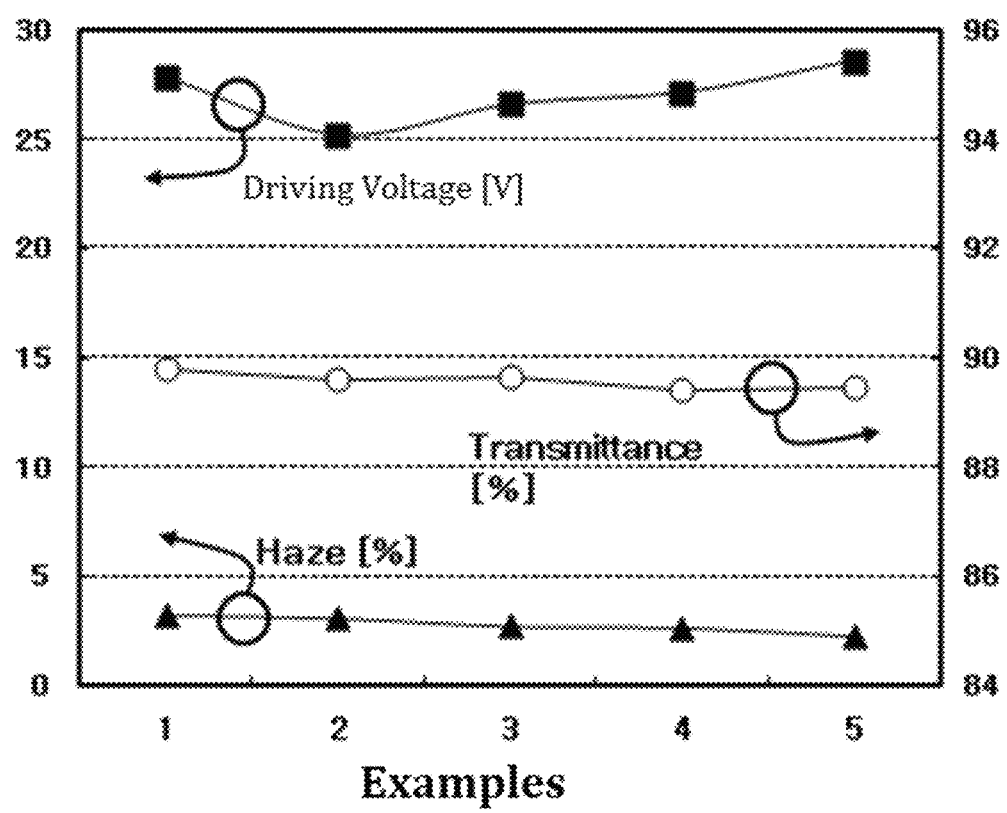
Figure 15:
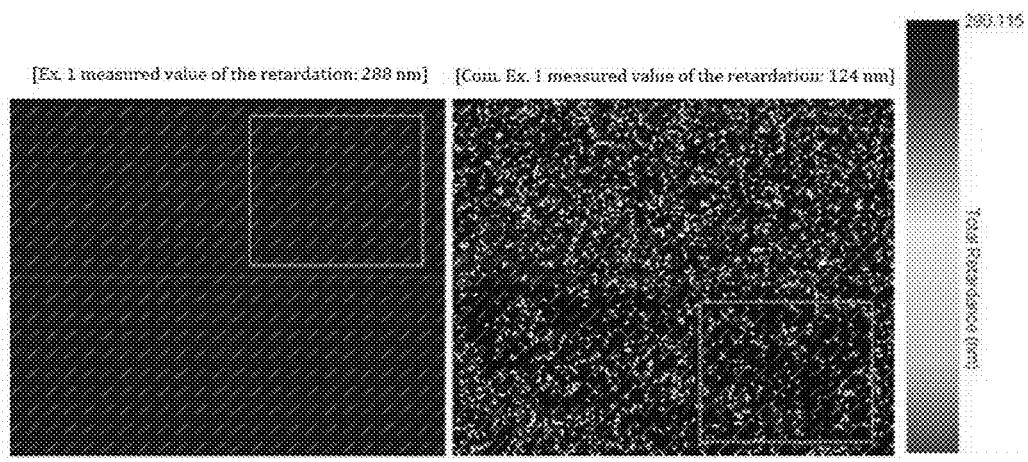

The retardation, haze and transmittance of the liquid crystal layers manufactured in Examples 1 to 5 were evaluated. Here, the retardation (measurement wavelength: 550 nm) was measured according to the manual of a manufacturer based on a wavelength of 550 nm using Axostep (Axometrics) equipment, and the haze and transmittance were also measured according to the manual of a manufacturer using a hazemeter (NDH-5000SP). Here, the retardation was evaluated in a state in which a voltage was not applied to the liquid crystal layer, and the haze and transmittance were evaluated by applying a driving voltage. FIG. 11 is a diagram showing results obtained by evaluating retardations with respect to Examples, and FIG. 12 is a diagram showing results obtained by evaluating haze and transmittance with respect to Example. FIG. 15 shows AXO-STEP measured data with respect to Example 1 and Comparative Example 1.

EXPERIMENTAL EXAMPLE 3

Figure 13:
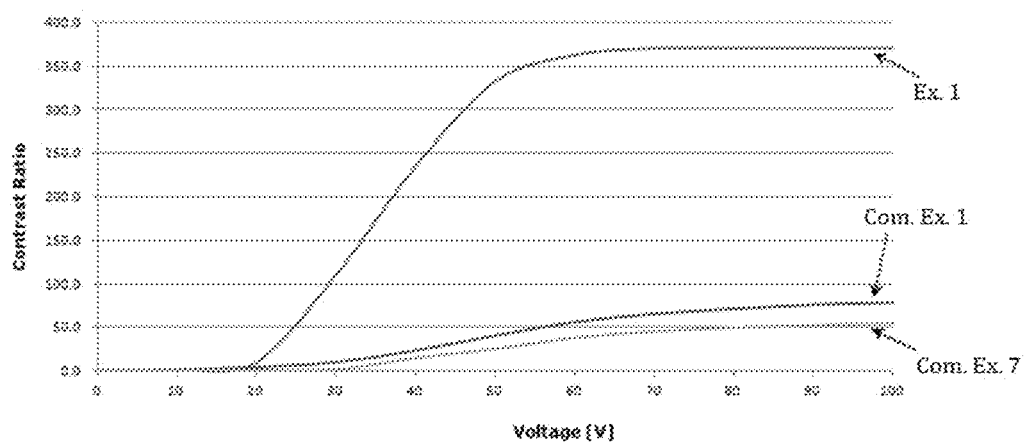

A contrast ratio was evaluated by evaluating a brightness by applying a voltage to the liquid crystal layers manufactured in Examples and Comparative Examples step by step. The brightness and contrast ratio were evaluated by converting values measured by LCMS-200 equipment (Sesim Photonics Technology). In the evaluation process, a distance between a measurement target and a light receiving part (detector) was maintained at approximately 10 cm, and a diameter of the light receiving part (detector) was approximately 1.5 mm FIG. 13 shows evaluation results for Example 1, and Comparative Examples 1 and 7. For evaluation, the liquid crystal layers of Example 1 and Comparative Example 1 were placed between two polarizing plates in which light absorption axes were perpendicular to each other, and in the case of Comparative Example 7 configured to be switched between a dispersing mode and a white (transmitting) mode, a contrast ratio between the dispersing mode and the transparent mode was evaluated without using a polarizing plate. As seen from the drawings, in Example 1, the maximum contrast ratio was 350 or more, in Comparative Examples 1 and 7, the contrast ratio was 100 or less. Meanwhile, the maximum contrast ratios in Examples 2 to 5 were all 350 or more, and the maximum contrast ratios in Comparative Examples 2 to 6, 8 and 9 were all less than 100.

EXPERIMENTAL EXAMPLE 4

Figure 14:
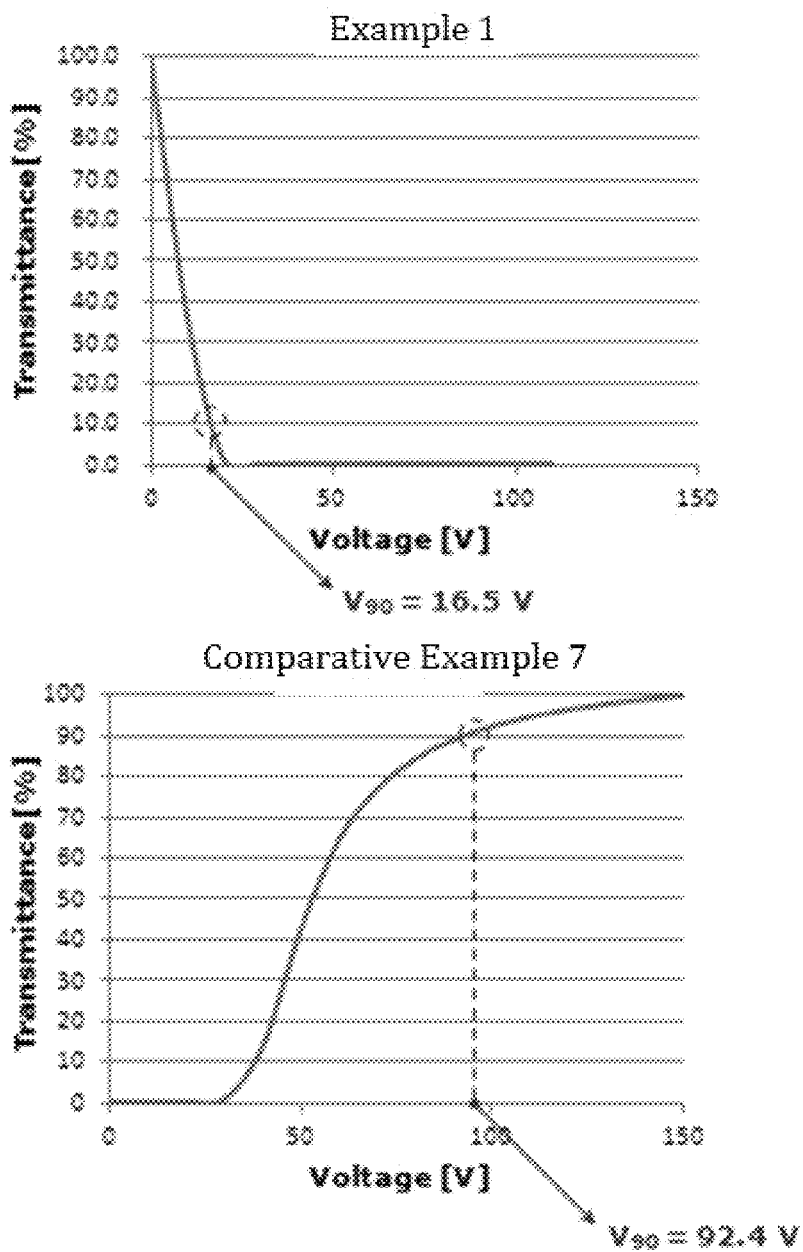

In Examples 1 and 7, a transmittance according to a driving voltage was evaluated. In Example 1, the device exhibiting a normally white mode was configured by disposing the liquid crystal layer between two polarizing plates in which light absorption axes were perpendicular to each other to be aligned at 45 degrees with the light absorption axis of the polarizing plate, and then the transmittance was evaluated by applying a voltage and switching a black mode, and in Comparative Example 7, a driving voltage was measured by applying a voltage to the device present in a normally dispersing mode to be converted into a transparent mode. FIG. 14 shows the measurement results, and as seen from FIG. 14, in Example 1, a driving voltage for exhibiting a transmittance of 10% was 16.5 V, and in Comparative Example 7, a driving voltage for exhibiting a transmittance of 90% was 92.4 V. Meanwhile, as the evaluation was performed in the same manner in Examples 2 to 5, the driving voltages for exhibiting a transmittance of 10% were all less than 30 V, in Comparative Examples 1 to 6, 8 and 9, the driving voltages for exhibiting a transmittance of 10% were all 90V or more.

EXPERIMENTAL EXAMPLE 5

Evaluation of Thermal Stability

Thermal stabilities of the liquid crystal layer (measured retardation: 288 nm) manufactured in Example 1 and the liquid crystal layer (measured retardation: 319 nm) manufactured in Comparative Example 6 were evaluated. Specifically, the thermal stability was evaluated by evaluating a retardation after each liquid crystal layer was maintained in an oven at 70° C. for 200 hours. Afterward, in Example 1, the minimum and maximum retardations were 254.4 nm and 278.9 nm, respectively, the average retardation was 263 nm, and a retardation change was 8.7%. In Comparative Example 6, the minimum and maximum retardations were 226.2 nm and 273.9 nm, respectively, the average retardation was 254.2 nm, a retardation change was 20.4%. In addition, as the result of evaluating thermal stabilities of Examples 2 to 5 in the same manner, the retardation changes were all less than 10%.

What is claimed is:

1. A polymerizable composition, comprising: a precursor of an alignable polymer network comprising a bifunctional acrylate compound, and optionally at least one selected from the group consisting of a multifunctional acrylate compound that is a tri-or more functional acrylate compound and a monofunctional acrylate compound such that they satisfy the Equations 1 to 3 below:

$$A \geq 1.3 \times B \quad \text{[Equation 1]}$$

$$A \geq C \quad \text{[Equation 2]}$$

$$A \geq 0.6 \times (B+C) \quad \text{[Equation 3]}$$

wherein the "A," "B" and "C" are weight ratios, respectively, between the compounds obtained after converting the sum of weights of the bifunctional acrylate compound, the multifunctional acrylate compound and the monofunctional acrylate compound in the precursor to be 100, wherein a value (A−1.3×B) obtained by subtracting 1.3×B from A is within a range of 0.5 to 100, and a value (A-C) obtained by subtracting C from A is within a range of 0 to 100, and a value (A−0.6×(B+C)) obtained by subtracting 0.6×(B+C) from A is within a range of 2 to 100, wherein the bifunctional acrylate compound is represented by Formula 1:

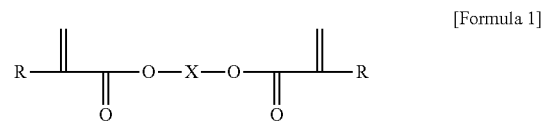

[Formula 1]

where the "R" is each independently hydrogen or an alkyl group having 1 to 4 carbon atoms, and the "X" is an alkylene or alkylidene group having 1 to 20 carbon atoms, wherein the polymerizable composition satisfies Equation B:

$$(1-a) \times \{(2n_0^2 + n_e^2)/3\}^{0.5} \leq n_p \leq (1+a) \times n_e \quad \text{[Equation B]}$$

where the "a" is a number within a range from 0 to 0.5, the "$n_o$" is an ordinary refractive index of the liquid crystal compound, the "$n_e$" is an extraordinary refractive index of the liquid crystal compound, and the "$n_p$" is a refractive index of the polymer network.

2. The polymerizable composition of claim 1, wherein the polymerizable composition comprises:
   5 to 50 parts by weight of the precursor of an alignable polymer network; and
   50 to 95 parts by weight of a liquid crystal compound.

3. The polymerizable composition according to claim 1, wherein the precursor satisfies the following Equations 4 to 6:

$$A \geq 40 \quad \text{[Equation 4]}$$

$$B \leq 30 \quad \text{[Equation 5]}$$

$$C \leq 50 \quad \text{[Equation 6]}$$

wherein the "A," "B" and "C" are weight ratios, respectively, between the compounds obtained after converting the sum of weights of the bifunctional acrylate compound, the multifunctional acrylate compound and the monofunctional acrylate compound in the precursor to be 100.

4. The polymerizable composition according to claim 1, wherein the precursor comprises a multifunctional acrylate compound represented by Formula 2:

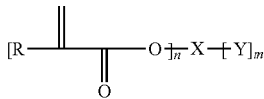

[Formula 2]

where the "n" is a number within a range of 3 or more, the "m" is a number within a range from 0 to 5, the "R" is each independently hydrogen or an alkyl group having 1 to 4 carbon atoms, the "X" is a (m+n) valent radical, and the "Y" is hydrogen or an alkyl group.

5. The polymerizable composition according to claim 4, wherein the "X" of Formula 2 is a (m+n) valent radical derived from a hydrocarbon having 2 to 20 carbon atoms.

6. The polymerizable composition according to claim 1, wherein the precursor comprises a monofunctional acrylate compound represented by Formula 3:

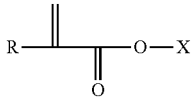

[Formula 3]

where the "R" is hydrogen or an alkyl group having 1 to 4 carbon atoms, and the "X" is an alkyl group having 1 to 20 carbon atoms.

7. The polymerizable composition according to claim 1, which satisfies Equation C:

$(n_e+n_o)/2-b \le \{(2n_o^2+n_e^2)/3\}^{0.5} \le (n_e+n_o)/2+b$ [Equation C]

where the "$n_e$" is an extraordinary refractive index of the liquid crystal compound, the "$n_o$" is an ordinary refractive index of the liquid crystal compound, and the "b" is a number within a range from 0.1 to 1.

8. The polymerizable composition according to claim 1, which is a solventless type.

9. A method of manufacturing a liquid crystal device, comprising:
forming a liquid crystal layer comprising an alignable polymer network and a liquid crystal compound in the alignable polymer network by polymerizing a layer comprising the polymerizable composition of claim 1.

10. The method according to claim 9, wherein the layer comprising the polymerizable composition is formed by roll coating, printing, inkjet coating, slit nozzling, bar coating, comma coating, spin coating, gravure coating or squeeze coating.

11. The method according to claim 10, wherein the layer comprising the polymerizable composition is formed by placing the polymerizable composition between two base layers, and applying a pressure to at least one of the base layers.

12. The method according to claim 10, wherein a solventless composition is used as the polymerizable composition.

13. The method according to claim 9, wherein the polymerization is performed while the layer comprising the polymerizable composition is in contact with an alignment layer.

14. The method according to claim 9, wherein the polymerization is performed while the polymerizable composition is maintained in a nematic phase.

15. The polymerizable composition of claim 1, wherein the precursor comprises a bifunctional acrylate compound represented by Formula 1:

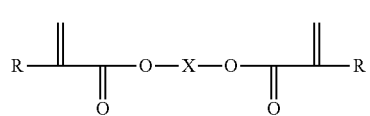

[Formula 1]

each "R" is independently hydrogen or an alkyl group having 1 to 4 carbon atoms, and the "X" is an alkylene or alkylidene group having 1 to 20 carbon atoms,
wherein the precursor comprises a multifunctional acrylate compound represented by Formula 2:

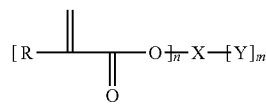

[Formula 2]

wherein "n" is 3 or more,
"m" is from 0 to 5,
each "R" is independently hydrogen or an alkyl group having 1 to 4 carbon atoms,
"X" is a (m+n) valent radical, and
"Y" is hydrogen or an alkyl group,
and wherein the precursor comprises a monofunctional acrylate compound represented by Formula 3:

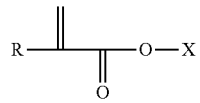

[Formula 3]

wherein each "R" is independently hydrogen or an alkyl group having 1 to 4 carbon atoms, and "X" is an alkyl group having 1 to 20 carbon atoms.

* * * * *